United States Patent [19]
Virtanen

[11] Patent Number: 6,030,581
[45] Date of Patent: Feb. 29, 2000

[54] LABORATORY IN A DISK

[75] Inventor: Jorma Virtanen, Irvine, Calif.

[73] Assignee: Burstein Laboratories, Irvine, Calif.

[21] Appl. No.: 09/064,636

[22] Filed: Apr. 21, 1998

Related U.S. Application Data

[63] Continuation of application No. PCT/US98/04377, Feb. 27, 1998.
[60] Provisional application No. 60/039,419, Feb. 28, 1997.
[51] Int. Cl.$^7$ .............................. G01N 15/06; C12Q 1/68
[52] U.S. Cl. ................. 422/68.1; 369/275.1; 369/275.3; 369/280; 369/282; 422/50; 435/4; 435/6; 435/7.1; 435/286.1; 435/286.5; 435/287.1; 435/287.2; 435/287.3; 436/501
[58] Field of Search ......................... 422/50, 68.1; 435/6, 435/7.1, 286.1, 286.5, 287.1, 287.2, 287.3, 4; 436/501; 935/77, 78; 369/275.1, 275.3, 280, 282

[56] References Cited

U.S. PATENT DOCUMENTS

| | | | |
|---|---|---|---|
| 4,756,971 | 7/1988 | Virtanen et al. | 428/405 |
| 5,061,381 | 10/1991 | Burd | 210/789 |
| 5,122,284 | 6/1992 | Braynin et al. | 210/782 |
| 5,160,702 | 11/1992 | Kopf-Sill et al. | 422/72 |
| 5,173,193 | 12/1992 | Schembri | 210/782 |
| 5,173,262 | 12/1992 | Burtis et al. | 422/72 |
| 5,186,844 | 2/1993 | Burd et al. | 210/782 |
| 5,242,606 | 9/1993 | Braynin et al. | 210/787 |
| 5,304,348 | 4/1994 | Burd et al. | 422/72 |
| 5,409,665 | 4/1995 | Burd | 422/64 |
| 5,413,732 | 5/1995 | Buhl et al. | 252/182.11 |
| 5,457,053 | 10/1995 | Burd et al. | 436/45 |
| 5,472,603 | 12/1995 | Schembri | 210/380.1 |
| 5,518,930 | 5/1996 | Burd | 436/45 |
| 5,591,643 | 1/1997 | Schembri | 436/45 |
| 5,874,214 | 2/1999 | Nova et al. | 435/6 |

FOREIGN PATENT DOCUMENTS

| | | |
|---|---|---|
| 0 417 305 A1 | 3/1991 | European Pat. Off. . |
| 0 707 076 A1 | 4/1996 | European Pat. Off. . |
| 0 721 016 A2 | 7/1996 | European Pat. Off. . |
| WO 93/20092 | 10/1993 | WIPO . |
| WO 93/22053 | 11/1993 | WIPO . |
| WO 96/09548 | 3/1996 | WIPO . |
| WO 96/32841 | 10/1996 | WIPO . |
| WO 96/35940 | 11/1996 | WIPO . |
| WO 97/21090 | 6/1997 | WIPO . |
| WO 98/01533 | 1/1998 | WIPO . |
| WO 98/07019 | 2/1998 | WIPO . |
| WO 98/28623 | 7/1998 | WIPO . |

OTHER PUBLICATIONS

Matthews et al., Analytical Biochem., vol. 169, pp. 1–25, 1988.

Schembri, et al., "Portable Simultaneous Multiple Analyte Whole–Blood analyzer for Point–of–Care Testing"—*Clin. Chem*—38(9):1665–1670 (1992).

*Primary Examiner*—Ardin H. Marschel
*Attorney, Agent, or Firm*—Albert P. Halluin; J. David Smith; Howrey & Simon

[57] ABSTRACT

An apparatus is described that includes an optical disk, adapted to be read by an optical reader, comprising a first sector having substantially self-contained assay means for localizing an analyte suspected of being in a sample to at least one, predetermined location in the first sector and a second sector containing control means for conducting the assay and analyte location information, with respect to one or more analytes suspected of being in a sample, accessible to the reader, wherein the presence or absence of the analyte at said location is determinable by the reader using the control means and the location information. Depending on the nature of the assay, the disk will include fluid storage means, fluid transfer means, such as one or more capillary ducts, valves, batteries, dialyzers, columns, filters, sources of electric fields, wires or other electrical conductive means such as metallic surface deposits and the like.

15 Claims, 14 Drawing Sheets

SAMPLE IN
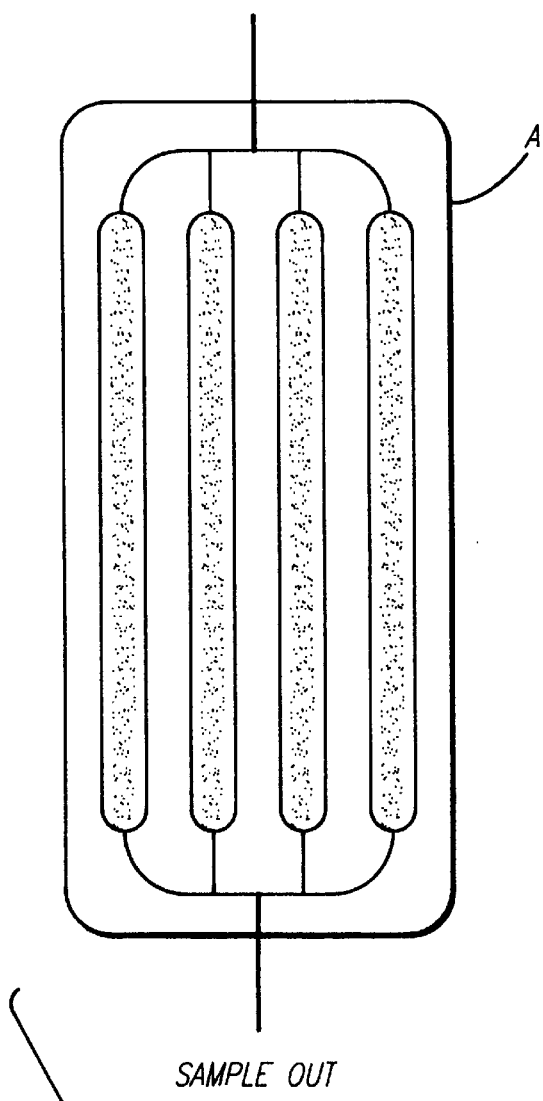
SAMPLE OUT
FIG. 10
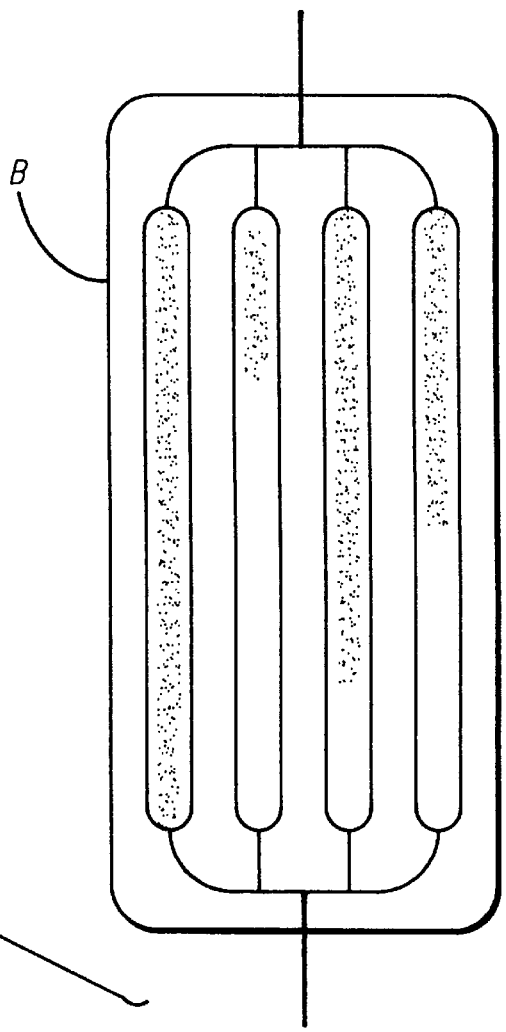

CUVETTE ASSEMBLY

ROTATE                STAND STILL
                      E-FIELD

START ROTATION        FRACTIONS ARE DIRECTED
                      FOR FURTHER PROCESSING

LABORATORY IN A DISK

The present application is a continuation of PCT/US98/04377 filed on Feb. 27, 1998 which in turn is a utility application based upon U.S. provisional application Ser. No. 60/039,419 filed on Feb. 28, 1997, abandoned.

FIELD OF THE INVENTION

This invention relates generally to diagnostic assays and methodology therefor. In particular, it relates to diagnostic assay components configured on a compact optical disk and methodology for the use thereof.

BACKGROUND

There is an enormous need to make clinical assays faster, cheaper and simpler to perform. Ideally patients should be able to test themselves, if so desired. One way towards this goal has been through miniaturization and integration of various assay operations. Currently, a number of bio-chip assays (so-called because some are built using silicon chip photolithography techniques) are commercially available or under development. All of these approaches require a reading machine and a computer.

Disk-shaped cassettes used for clinical assays in conjunction with UV/Vis spectrometry are also commercially available. U.S. Pat. No. 5,122,284 describes a centrifugal rotor that contains a number of interconnected fluid chambers connected to a plurality of cuvettes. The rotor is adapted to be utilized with a conventional laboratory centrifuge, and is formed of materials that allow photometric detection of the results of assays that have been carried out in the reaction cuvettes. A large number of rotor configurations and related apparatus for the same or similar types of analysis have been described. See for example U.S. Pat. Nos. 5,472,603; 5,173,193; 5,061,381; 5,304,348; 5,518,930; 5,457,053; 5,409,665; 5,160,702; 5,173,262; 5,409,665; 5,591,643; 5,186,844; 5,122,284; 5,242,606; and patents listed therein. Lyophilized reagents for use in such systems are described in U.S. Pat. No. 5,413,732.

The principles of a centrifugal analyzer have been adapted into a disk that can be used in a CD-drive like instrument (Mian, et al., WO 97/21090 Application). Mian teaches a modified CD-drive with a dual function: 1. It is used to read information stored in the disk, and 2. It is used to rotate the disk. However, Mian does not teach utilization of the reading capability of a CD-drive for actual assay analysis.

Notwithstanding recent advances, there remains a need for a simpler assay configuration that performs assays quickly, efficiently, accurately and at low cost. The present invention combines diagnostic assays with computers and compact disk technology. In its most preferred embodiment, a computer with a compact disk reader is the only instrument needed. All chemistry is performed inside a compact disk that may be referred to as an integrated biocompact disk (IBCD). The same compact disk is also encoded with software, i.e., machine-readable instructional and control information, that provides instructions to a computer prior to, during and after the assay.

CDs or DVDs represent the most economical and in many ways best information storage media. It must be noted that CD and DVD are currently used acronyms that may change in the future even if the underlying technology stays basically the same. A CD- or DVD-drive is in several respects equivalent to a scanning confocal microscope. At the same time these instruments are comparable to good centrifuges, because in commercial drives the rotation frequency is between 200–12,000 rpm and can be adjusted within certain limits. Combining these three features into the same analytical system results into great simplification as compared with any other analytical technique. Yet, the performance is comparable or better than in most competing methods. Although this invention requires slightly modified CD- or DVD-drives, it is possible to incorporate these changes into commercial drives. This will enable Point-Of-Patient-Care (POPC) and home use of this invention. Use of CD- or DVD-drives will allow accurate digital analysis of any sample without any specific analytical instrumentation.

SUMMARY OF THE INVENTION

In one aspect, the invention is directed to an optical disk, adapted to be read by an optical reader, comprising a first sector having a substantially self-contained assay means for binding an analyte suspected of being in a sample to at least one predetermined location in the first sector and optionally a second sector containing control means for conducting the assay and analyte location information, with respect to one or more analytes suspected of being in a sample, accessible to a reader, wherein the presence or absence of the analyte at said location is determinable by the reader using the control means and the location information. Depending on the nature of the assay, the disk may include fluid storage means, fluid transfer means, such as one or more capillary ducts, valves, batteries, dialyzers, columns, filters, sources of electric fields, wires or other electrical conductive means such as metallic surface deposits and the like.

The disk may have one or more sample entry ports to deliver sample fluid to the assay sector. Such ports if present are preferably sealable so that after application of the sample to the disk, the sealed disk including the sample comprises a hermetically sealed device that may be conveniently disposed of by conventional means or other disposal mechanisms for dealing with biological waste. Also, the assay sector of the disk is conveniently divided into various subsections for sample preparation and analyte separation. A waste receptacle subsection may be conveniently provided as well. The assay sector may be divided into a multiplicity of subsectors that each receives a sample. Each such subsector may analyze for one or more analytes depending on the particular application at hand.

In another aspect the invention is directed to an apparatus for conducting an assay comprising an optical disk, a disk reader and an information processor, the disk comprising a first sector having substantially self-contained assay means for localizing an analyte suspected of being in a sample to at least one, predetermined location in the first sector and optionally a second sector containing control information for conducting the assay and analyte location information, with respect to one or more analytes suspected of being in the sample, accessible to the reader and processable by the information processor, wherein the disk is adapted to be read by the reader and the information processor is adapted to determine the presence or absence of the analyte at said location using the control information and the location information. The apparatus may include a reader having a CD-ROM or DVD reader and an information processor, such as a personal computer.

In still another aspect the invention is directed to an optical disk, adapted to be read by a CD-ROM or DVD reader, comprising a substantially self-contained assay means in the disk for localizing an analyte suspected of being in a sample to at least one, predetermined location on the disk and means at said location for detection of the absence or presence of the analyte by the CD-ROM or DVD reader.

BRIEF DESCRIPTION OF THE DRAWINGS

FIG. 10 is a schematic representation of an array of linear assay sites that are conveniently located in a flow channel in the assay sector of the disk of this invention.

FIG. 14e (rightmost) is a schematic representation of the assay element in FIG. 14d after the spacer molecules have been cleaved. The reporter element is detached from the disk surface and free to be washed away from its discrete site.

DETAILED DESCRIPTION OF THE INVENTION

Figure 1:
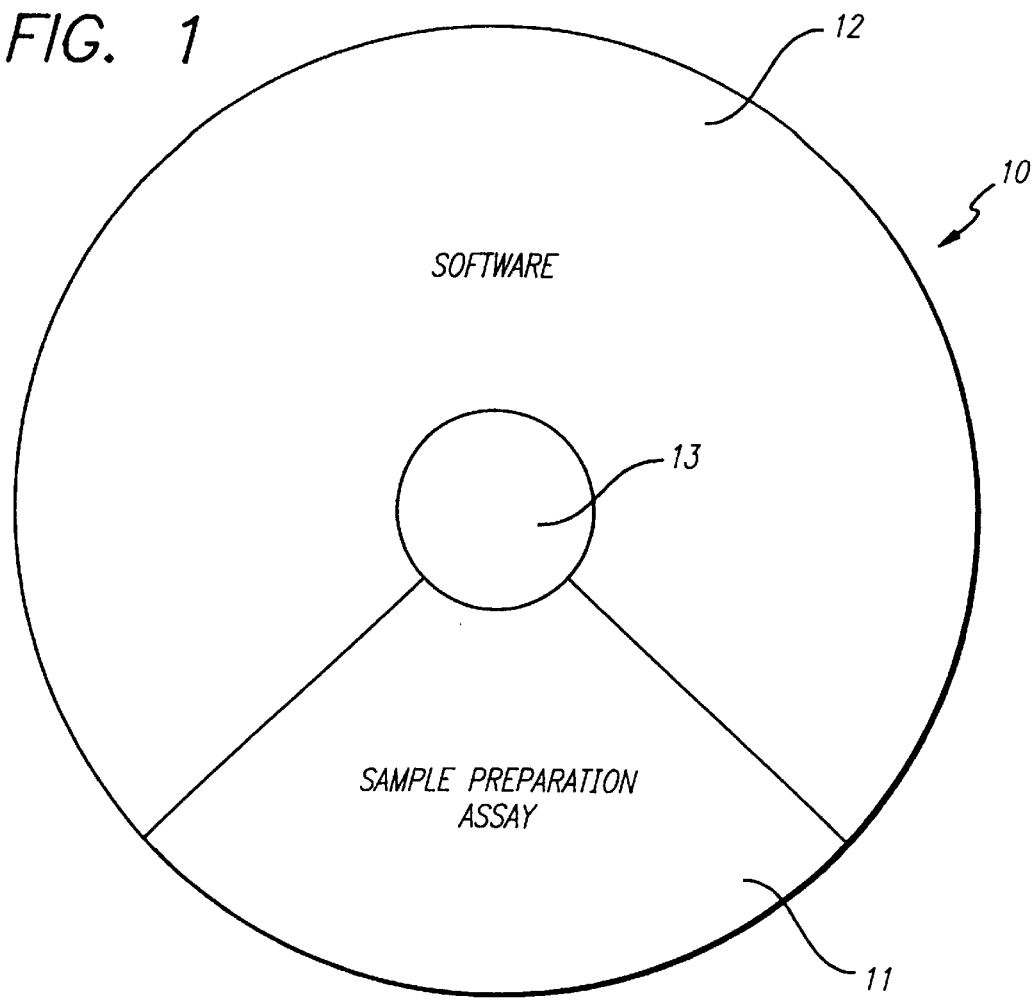
FIG. 1 is a schematic representation of a disk of this invention.

A schematic overall representation of an integrated bio-compact disk (IBCD) is set forth in FIG. 1. The disk (Bio-Compact Disk, BCD) may be virtually of any shape and size. For most practical applications it is circular having a diameter of 10–1000 mm, most advantageously 20–200 mm and a thickness of 0.1–20 mm, most advantageously 0.5–3 mm. The disk 10 contains two sectors: an assay sector 11 and a software sector 12. A central hole 13 is provided for location in a compact disk reader. Software for controlling the assay may be on a separate disk. However, it is preferred to have the software on the disk associated with an assay for a particular analyte or analytes to minimize the opportunity for human error when performing the assay. The possible components and unit operations of the IBCD are presented in the following description.

The disk rotates typically up to 16,000 rpm in conventional CD-ROM or DVD readers. In all CD-ROM and DVD readers the speed is adjustable within certain limits (200–16,000 rpm). However, for some operations it may be advantageous to utilize rotations at differing speeds, for example 1000–10,000 rpm, and most preferably 2000–5000 rpm. For any particular assay, the controlling software dictates the rotation regimen during the analysis. This regimen, the speeds and timing, including times in which perhaps no rotation occurs to allow for incubation, electrophoresis, isoelectric focusing, etc., is controlled to deliver reagents and sample to appropriate sites on the assay sector as dictated by the assay protocols. Available rotational speeds do allow for a significant centrifugal force that may be used to move liquids. Another energy source that may be easily used in the IBCD is chemical energy. A most suitable form of chemical energy is released by a battery in the form of electrical energy. Mechanical and chemical energy allow the operation of many kinds of components. Important components of a IBCD may include one or more of the following: capillaries, containers, filters, dialysis membranes, chromatographic columns, electrophoretic gels, valves, any micromechanical or electronic components including microprocessors, electrodes, especially enzyme electrodes, cuvettes, and assay elements. The possible unit operations carried out by the components include the following: centrifugation, filtering, transfer of liquids, mixing of liquids, dialysis, column separations, heating, cooling, electroconvection, electrophoresis, and analyte detection and signaling thereof.

Figure 5:
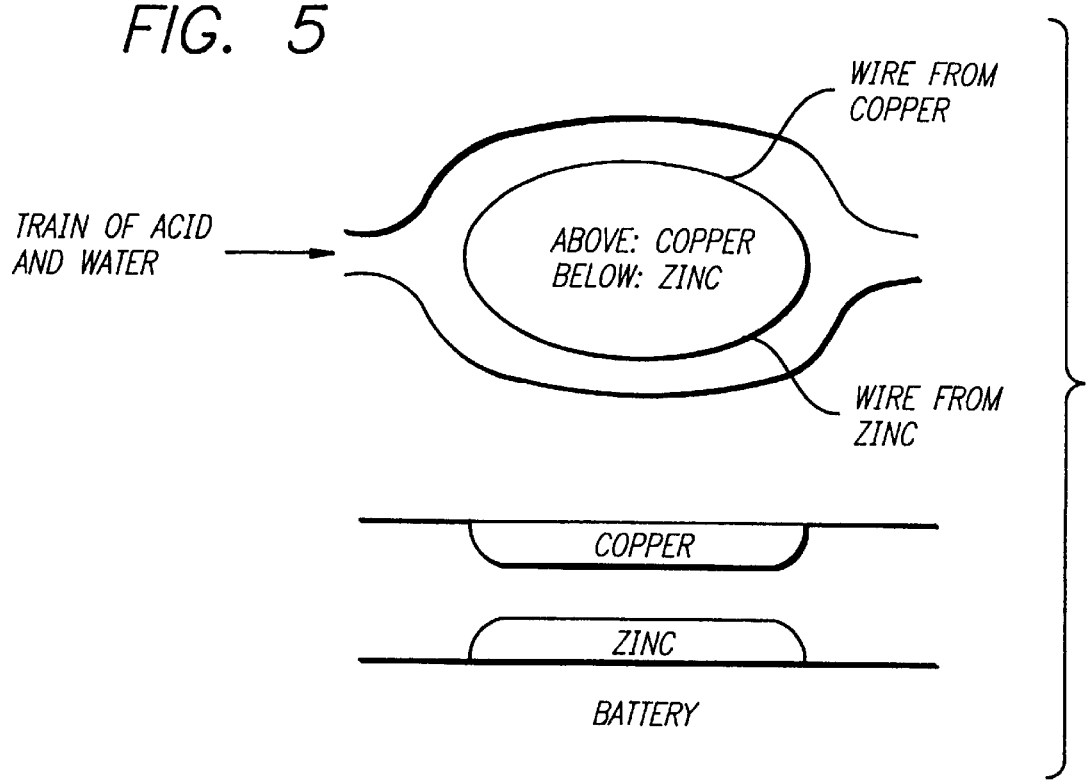
FIG. 5 is a schematic representation of a chemically actuated battery useful in the present invention.
Figure 9:
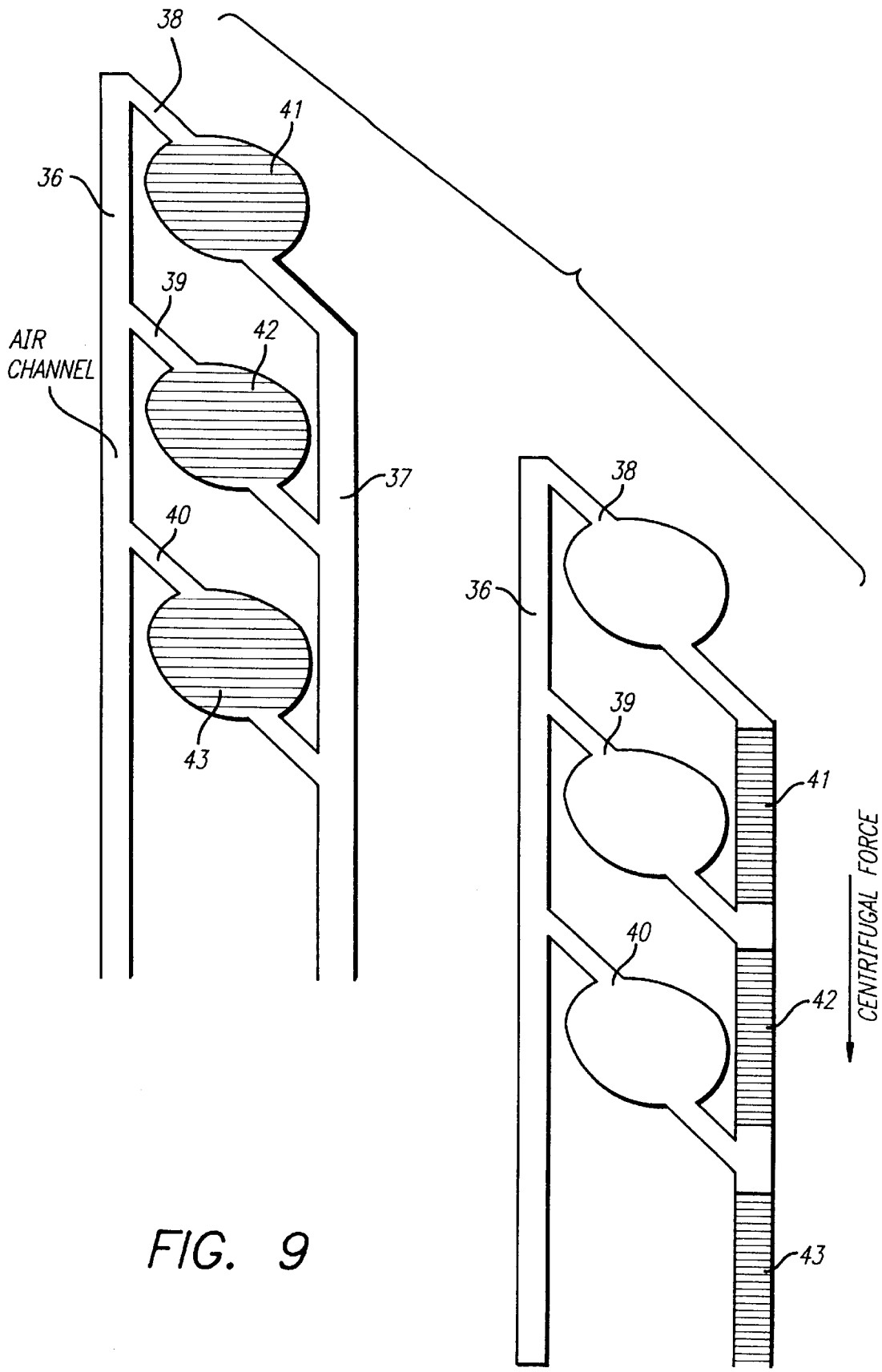
FIG. 9 is a schematic representation of a reagent train configured in joined capillary ducts that is useful in the present invention.

The IBCD is conveniently made from two pieces comprising upper and lower halves. The lower half may contain almost all the components, while the upper half may be a flat cover containing only a few components, such as electrodes and wires. The number of layers in this invention may be more than two and many components may also be pre-made as modules. Especially reagent containers, cuvette assemblies, columns, micromechanical components, light sources, and microprocessors are advantageously assembled as modules. Various features may be printed onto the soft plastic. Various components may be glued, either by thermal or UV-curing, melted together, connected by complementary mechanical features, mechanically clamped or simply enclosed inside a larger component. Some areas may be treated, for instance, with ammonia plasma to render these areas hydrophilic. The surface may be further treated by various molecules that render the surface inert or alternatively give it specific adsorption properties. Silylation is a general method for the treatment of surfaces (Virtanen, J. A., Kinnunen, P. K. J. and Kulo, A., "Organosilanes and their hydrolytic polymers as surface treatment agents for use in chromatography and electronics," U.S. Pat. No. 4,756,971). Covalent attachment of detergents will reduce the adsorption of proteins, such as albumin, and will also reduce the adsorption of soluble proteins. Metal electrodes and wires may be evaporated onto desired areas. Masks or resists may be used to localize the plasma treatment or metal deposition. Capillary ducts and fluid storage and retention compartments may be machined into the optical disks or formed by chemical means or in injection molding operations. As shown with reference to FIG. 2, the assay sector may contain a sample inlet port 14. The sample port is preferably sealable so that at the disk is effectively sealed, except for necessary venting to allow for fluid flow, to protect from any biological hazards. By various means, e.g. centrifugal force and like means that are well known in the art, a portion of the sample is metered to a sample preparation site 15, that may contain reagents and the like in order to conduct the assay. Alternatively, or in conjunction with reagents already in the sample preparation segment, a reagent train 16 may be provided to deliver, as needed, the necessary reagents in the proper order to the sample preparation segment. Additional details of the reagent train are shown in FIG. 9. It may be necessary to separate the analyte from the sample, at least partially, and this may be done in a sample separation segment designated generally as 17. A battery 18 is provided if electrical energy is required for the separation process. Additional details of the battery are shown in FIG. 5 and described below. The resultant sample is then transferred to the assay site 19. In a preferred embodiment of the invention, the assay site contains an assay element as described in greater detail below. The analyte binds to a predetermined location on the disk if it is present in the sample, and the presence of the analyte is detected by the reader from information that identifies the particular analyte with the location at which it is bound. A waste compartment is provided to collect overflow of reagents or sample that exceeds metered amounts for use in the assay and the various compartments and fluid transfer channels are vented appropriately to allow for fluid flow throughout the surface of the assay sector.

Figure 3:
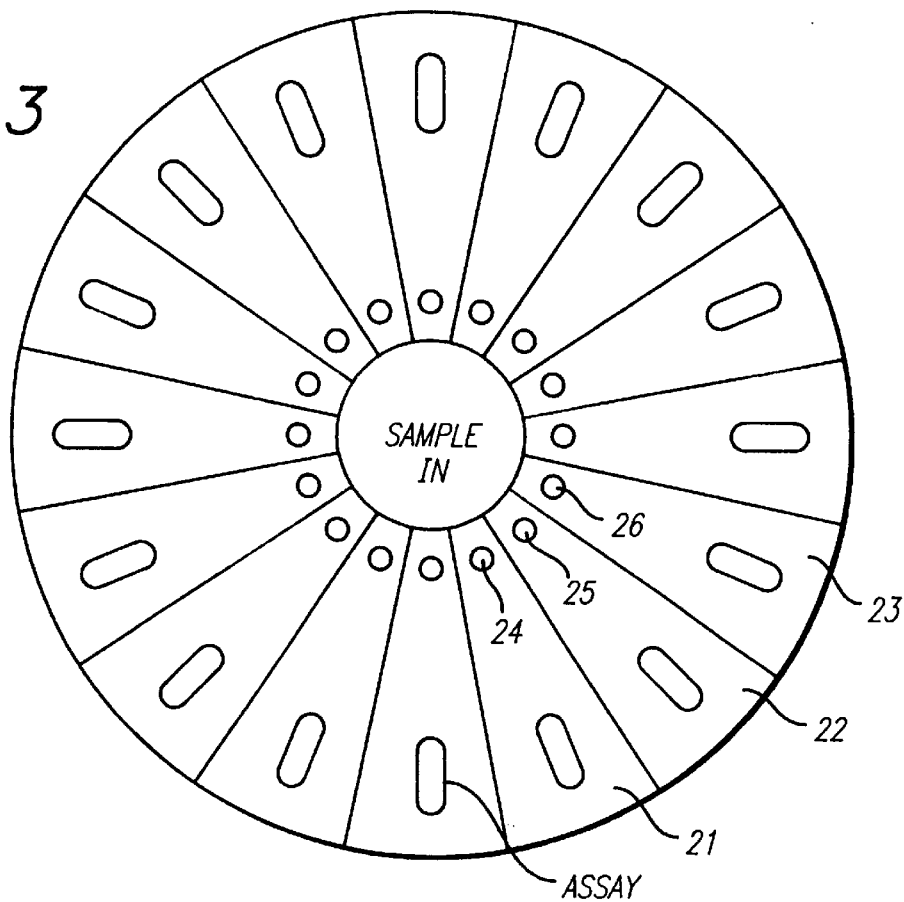
FIG. 3 is a schematic representation of a disk of this invention illustrating a multiplicity of assay sectors, each having an individual sample inlet port.
Figure 4:
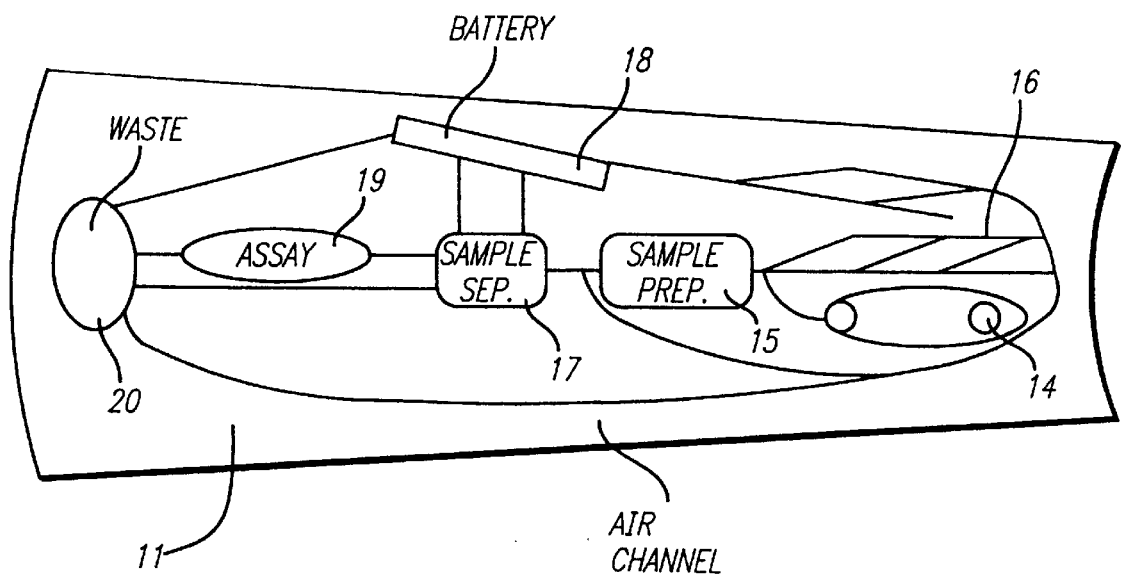
FIG. 4 is a more detailed schematic representation of one of the assay sectors illustrated in FIG. 3.

In one embodiment of the invention, a multiplicity of assay sectors 21, 22, 23, etc. as shown in FIG. 3 may be provided, each sector connected to an individual sample inlet port 24, 25, 26 respectively. The operation of each sector is substantially as described above although different assays may be conducted at the same time in individual sectors either for a multitude of analytes or a multitude of patients. The details of a particular sector are shown in greater detail in FIG. 4, where the various possible components are identified by the same numbers as used in the foregoing description.

Components

As shown in FIG. 5, a battery may be provided that consists simply of two metal layers, such as copper and zinc, which are in the lower and upper half, respectively. During storage they are separated by air. When the disk is rotated, the space between these two metals is filled by dilute mineral acid, depending on the nature of the metal electrodes. In the case of copper and zinc, this may be dilute sulfuric acid, containing copper ions and the battery is activated. This battery generates a voltage of 1.5 V for only about 1 hour. However, this is more than enough to complete the analysis. Longer lasting batteries may be made, if necessary, from other materials or thicker metal layers. Importantly, allowing water to flow into the space between the metal layers deactivates the battery. The activation and deactivation cycle may be repeated several times. Several batteries may be coupled in series to increase the potential, if necessary. Optionally, photodiodes may be included into the circuitry. In this case, the computer controlling the assay is provided with information about the active circuits. Also, a miniaturized, pre-fabricated battery may be utilized and activated by closing the electrical circuit with a salt, e.g. sodium chloride, solution.

Capillaries preferably are used to transfer liquid and air. Also, very small volumes of liquid may be stored in capillaries. Preferably, air capillaries are hydrophobic, while capillaries that come into contact with water are hydrophilic. As necessary, capillaries may have circular or rectangular cross-sections. Typical depths are between 10 $\mu$m and 500 $\mu$m, while widths are between 50 $\mu$m and 2 mm. Air capillaries utilize the larger dimensions to prevent any formation of a pressure gradient, unless otherwise desired. The velocity of the flow depends on the frequency of the rotation of the IBCD, the dimensions of the capillary and the viscosity and density of the liquid. Physical properties of the liquid are dictated by the assay and the frequency of rotation is limited to a certain extent by the CD-ROM or DVD reader. Thus, the dimensions of the capillary are used to adjust the speed of the liquid transfer. The capillary ducting may be provided with "bottlenecks," i.e., restrictions in the cross-sectional areas of the capillary, to control the velocity of the liquid as necessary. Hydrophilicity and hydrophobicity may be used for the same purpose.

The exact dimensions of the capillary network and chambers may be designed by using the Navier-Stokes equation:

$$\rho v = \rho b - \nabla p + \mu \nabla^2 v$$

where $\rho$ is the density, p is the pressure, v is the velocity, b is the body force field, $\mu$ is the viscosity and $\nabla$ is the differential operator del (Mase, Continuum Mechanics, McGraw-Hill, 1970). Pressure is a scalar field, while v and b are vector fields. Commercial computer software for solving of the Navier-Stokes equation in complicated geometries is available.

Containers or compartments formed in the disk are used for sample input, to store reagents, to perform reactions and to collect waste. Their depth is about 1–2000 $\mu$m, preferably about 10–800 $\mu$m and they may have any shape possible, although circular or rectangular cross-sections are preferred. Compartments are hydrophilic, except for one end of the waste container which has an air capillary that is hydrophobic. Reaction compartments may be formed with electrodes for heating, electroconvection of electrochemical purposes. Electrodes are preferably evaporated gold films. Compartments may also have valves that are operated by electricity or chemically as described below. Storage containers may be metal coated, preferably gold coated, to prevent the penetration of the water into the plastic. Reagents may also be prepacked into cassettes, which are virtually impermeable. These cassettes may be closed during storage and opened manually, by puncturing or by opening a valve or plug when the sample cassette is place in the disk. Opening of the cassette may also be facilitated by centrifugal force when the IBCD starts to rotate. In any case, proper liquid flow is maintained during the assay by computer control via CD or DVD-reader.

The liquid flow during the assay may be monitored by using a reflective element. The reflective element utilizes the laser that is in the CD or DVD-reader and the fact that even when the liquid is transparent its reflective index is significantly different from that of air. Thus the laser light is reflected back to the CD or DVD-reader in the presence of air and in some other direction in the presence of liquid, or vice versa. Another method of monitoring the liquid flow is to use an active light source, such as an LED or semiconductor laser. Such a light may be powered by the presence of an electrically conductive liquid, such as plasma or buffer, acting to close an electronic circuit.

A LC-display may be used to transmit information from the IBCD to the CD or DVD-drive and to the computer. LC-display may have a large number of pixels that reflect light when there is a potential over the LC-filin. These pixels may be, for instance, linearly organized, so that in one end low potential is needed for the reflection of the light, while on the other end the potential must be much higher for the same result. A CD or DVD-drive is able to localize the reflective pixels and accordingly, the potential in the circuit can be measured. Potential change can be due to an electrochemical process in one of the electrochemical cells. For example, an electrode coated with cholesterol oxidase will generate hydrogen peroxide in the presence of cholesterol. Hydrogen peroxide will change the potential of the circuitry and cholesterol may be quantitated.

Filters may be used to remove large particles, such as cells, dust, etc. from the soluble sample. Accordingly, filters are most preferably included as part of the sample inlet compartment. Filters may be formed from porous plastic, glass, cross-linked cotton or cellulose, etc. These materials may be in the shape of rods or similar shapes depending on the particular use to which they are being put. Plastics, such as Teflon, may be used as films.

Figure 6:
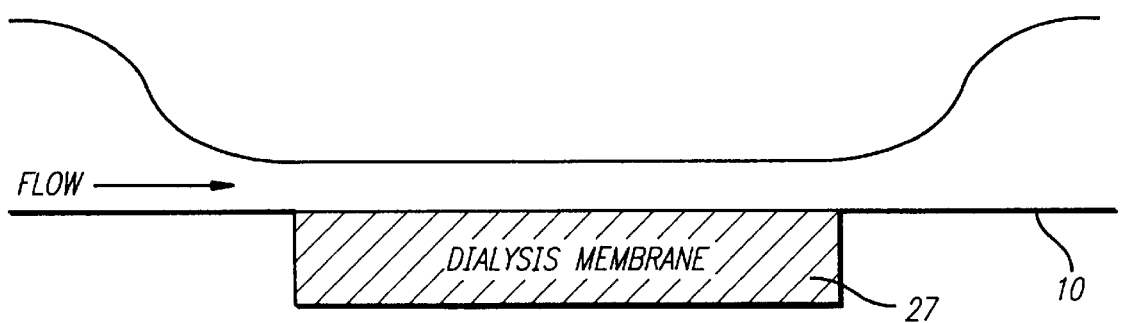
FIG. 6 is a schematic representation of a structure to provide a dialysis function in the disk of this invention.

Since chaotropic agents are often used to denature oligonucleotides during sample preparation, it is advantageous to provide a means of dialysis in the disk to remove the salt prior to the assay being performed. As shown in FIG. 6, a dialysis unit is prepared by putting a dialysis membrane 27 on either one or both halves (top and bottom) of a compartment formed in the disk 10. Taking into account the small volumes, the buffer that is already inside the dialysis membrane is usually sufficient and typically no buffer is needed on the side of the membrane opposite the fluid layer.

Figure 7:
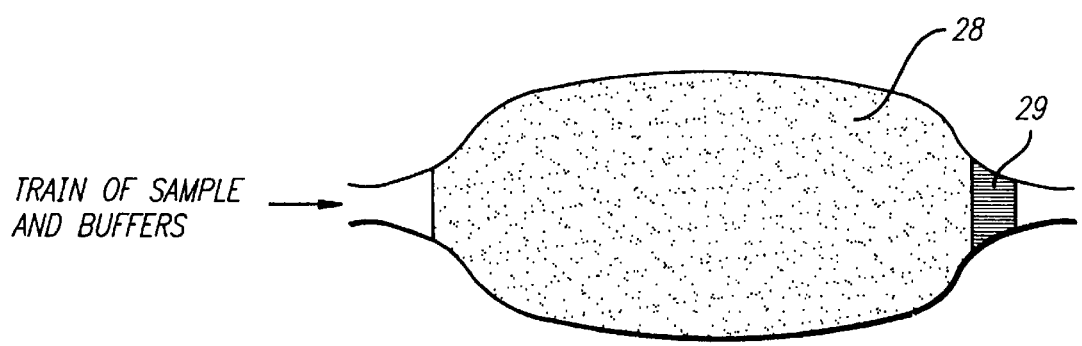
FIG. 7 is a schematic representation of a column that may be included in the disk of this invention.

A column may be prepared, such as shown in FIG. 7, by filling a compartment 28 with a desired gel, adsorbent or ion exchanger, e.g. silica gel, Sephadex, etc. (the particular material is chosen for the particular application for which it is used) and putting a filter 29 in the other end. Examples of potential uses, include separating smaller molecules from larger ones and fractionating hydrophilic and hydrophobic compounds. An ion exchange column is especially useful for the separation of nucleic acids from other biomolecules. The columns lend themselves to other uses that may be convenient or necessary for conducting any particular assay.

Figure 8:
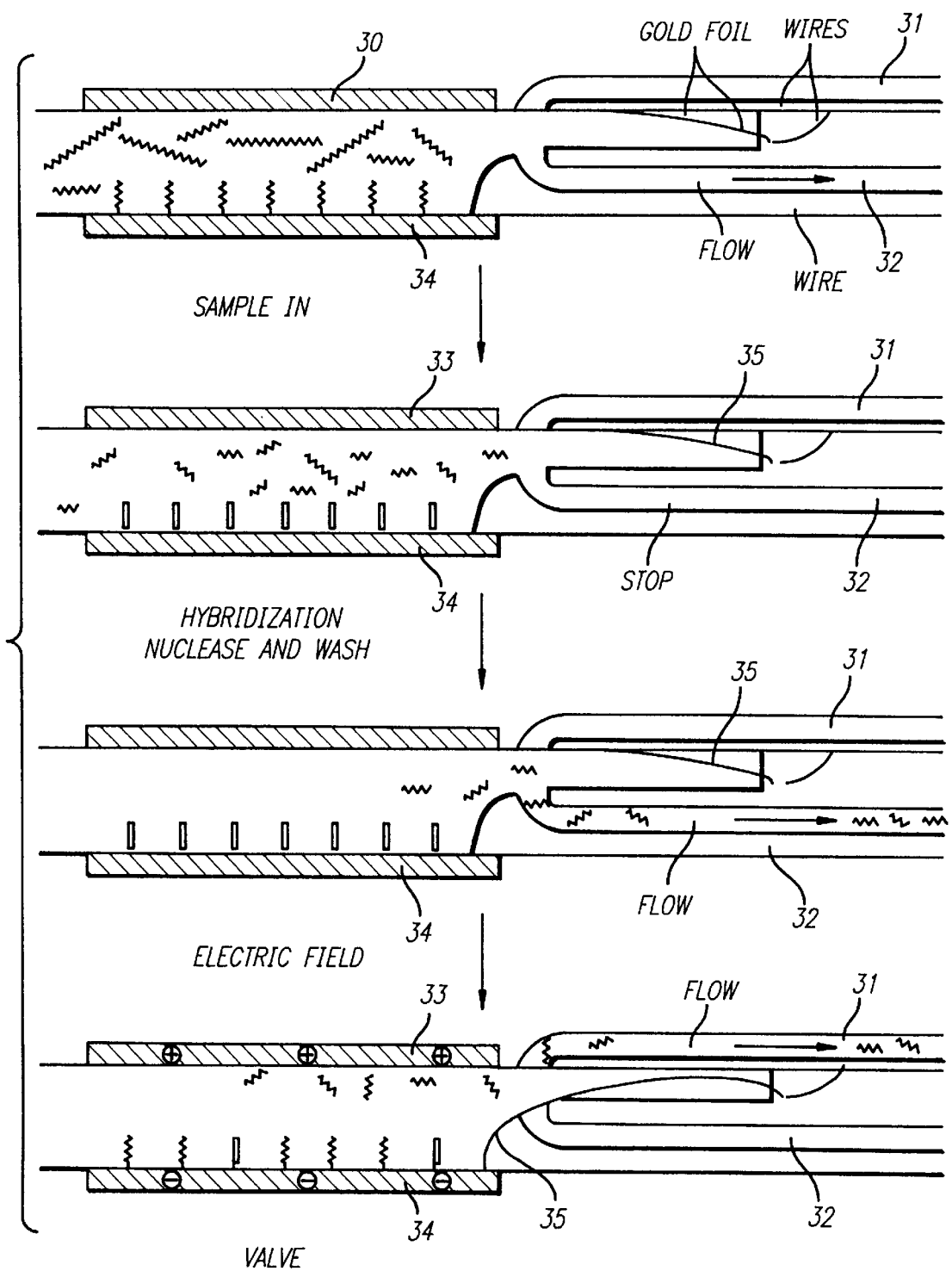
FIG. 8 is a schematic representation of an electrically controlled valve useful in the present invention.

FIG. 8 illustrates a valve, designated generally as 30, that may be located in one end of a column or a reaction container, which has two outlet capillaries 31 and 32. In addition, there are two electrodes, 33 and 34, which are not charged initially at the position illustrated and a conductive, metallic foil 35 that is adapted to close one or the other of the capillaries depending on its position relative to each capillary. The metal foil is biased to close one of the capillaries when no current is flowing and operates to open the previously closed capillary and close the other capillary when current flows. As an example, the valve is made from a thin gold foil, which is mechanically pressed against the other outlet capillary and is electrically connected to the closest electrode. When the battery is activated the gold foil is repelled by the closest electrode and attracted by the other electrode. As a result the gold foil is pressed against the other outlet. Other conductive metallic foils may be used, but a metal that is conductive and non-corroding is preferred for most operations. The battery may be deactivated as explained earlier and the valve is then switched back to its original position.

The laser of CD-R or CD-RW-drives has power up to 10 mW that can heat objects to high temperatures, even to 600° C. The power is strong enough to puncture holes in several materials, including plastics. Plastic should contain a dye that absorbs the laser light. Thermal expansion may be used for reversible valving. For instance, the bending of bimetallic foils is extremely sensitive to the temperature.

Piezoelectric material may be used as a valve. Piezoelectricity may also be used for measuring extremely small volumes of liquids, for example nanoliters of the sample can be divided between different assays.

Valve-like operations may also be performed chemically by deposition from solution of a solid chemical compound and/or dissolution of a deposited, solid compound. The first outlet of such a valve is closed by deposition of a chemical compound inside the capillary. The compound may be, for example, silver chloride. The chloride ions may be in the main fluid stream while in separate side capillaries are pure water and silver nitrate in water. The side capillaries are configured such that first the water and then the silver nitrate are added to the main fluid stream containing the chloride. The moment the silver ions arrive at the intersection it is clogged, effectively acting as a closed valve. Alternatively, a capillary may be initially clogged by the solid form of a soluble compound, such as sodium chloride. Addition of any aqueous solution dissolves the sodium chloride clog and the capillary is opened.

Figure 13:
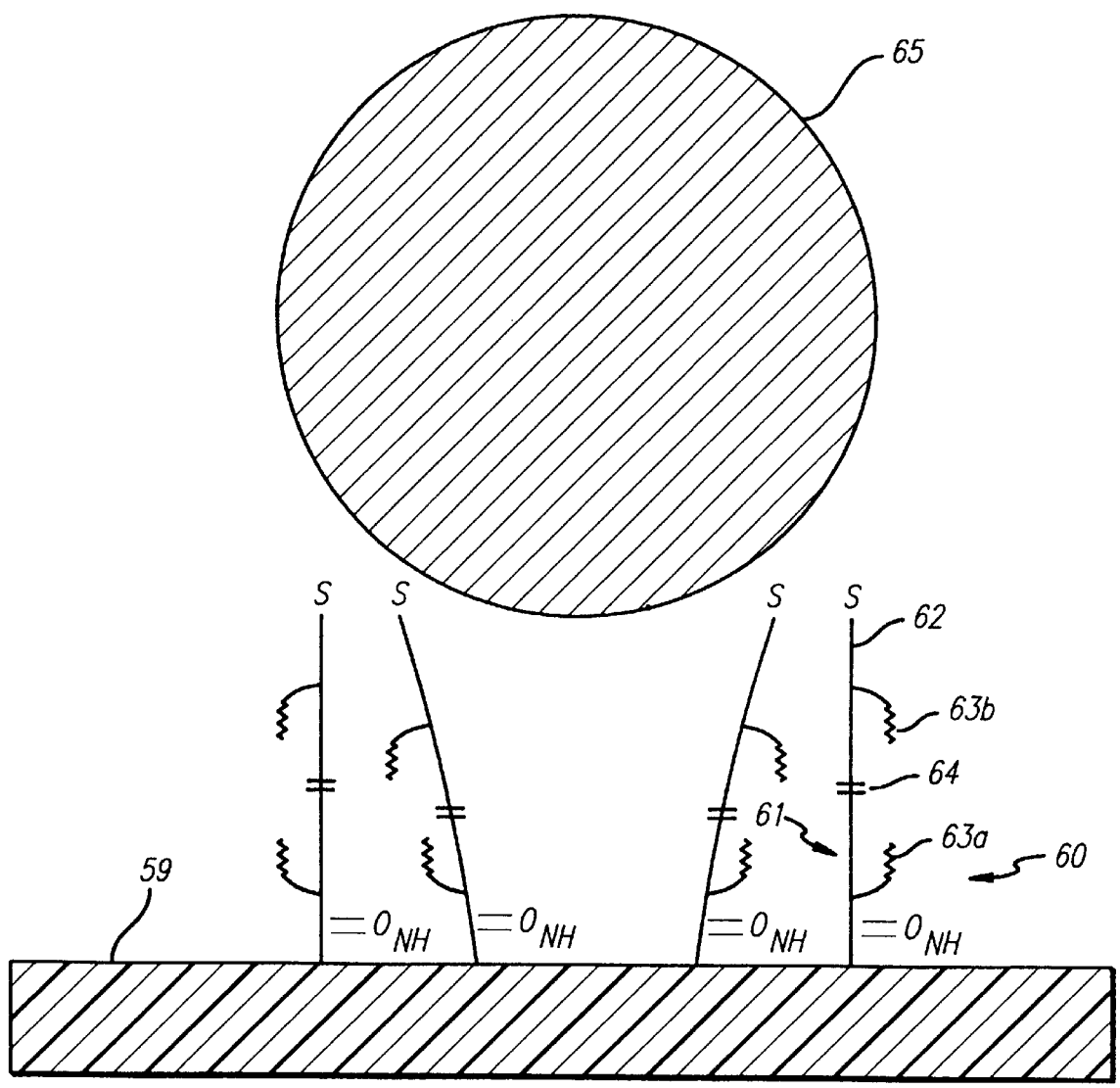
FIG. 13 is a schematic representation of an assay element of the invention illustrating the spacer molecule, with component sidearms and cleavage site, bound to a disk surface at one end and to a reporter element (gold or latex sphere) at its other end.
Figure 14A:
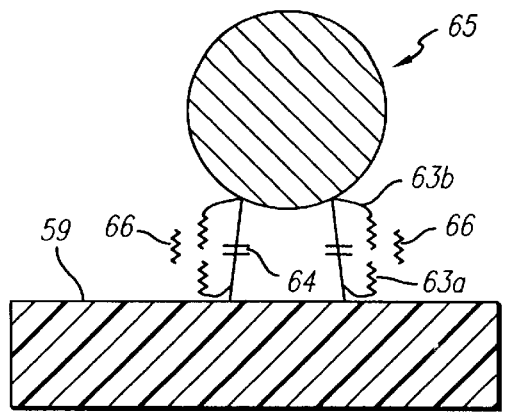
FIG. 14a is schematic representation of a first assay element of this invention, at an early stage during the assay procedure.
Figure 14B:
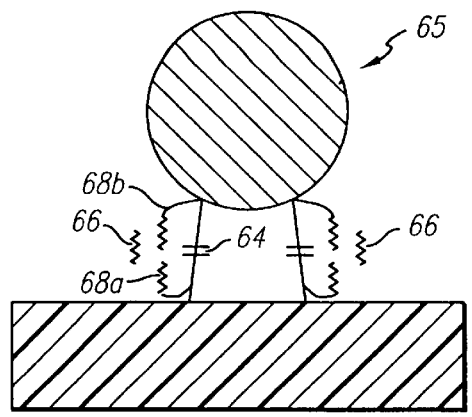
FIG. 14b is schematic representation of a second assay element of this invention, at an early stage during the assay procedure.
Figure 14C:
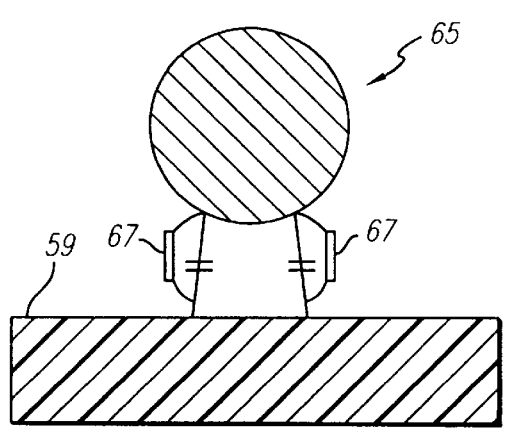
FIG. 14c is a schematic representation of the assay element in FIG. 14a wherein analyte molecules have bound the sidearms forming a connective loop between the sides of the cleavage site.
Figure 14D:
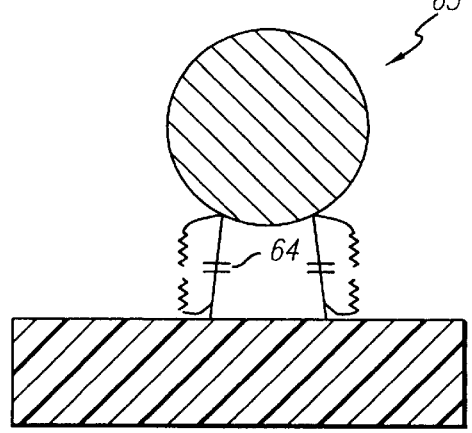
FIG. 14d is a schematic representation of the assay element in FIG. 14b wherein analyte molecules have not bound to the sidearms and no connective loop has formed between the sides of the cleavage site.
Figure 14E:
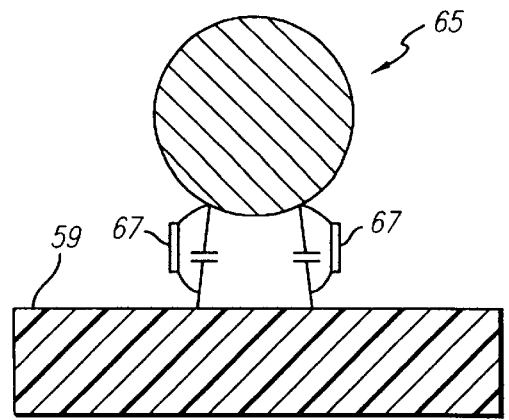
FIG. 14e (leftmost) is a schematic representation of the assay element in FIG. 14c after the spacer molecules have been cleaved. The reporter element remains attached to the disk surface at a discrete site.
Figure 14F:
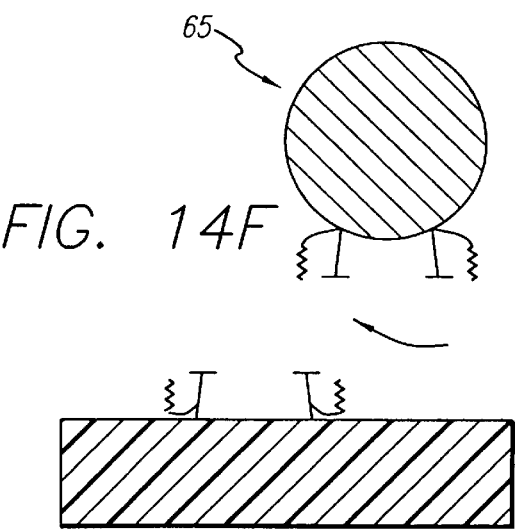

The assay element is preferably utilized in the assay site of the present invention. Briefly, the assay element (FIG. 13) includes a cleavable spacer 61 covalently attached at one end 60 to the disk surface 59 and at the other end 62 to a reporter element 65. The preferred embodiments of the reporter element described herein include reflective gold spheres or opaque latex spheres. Also included are two recognition elements 63a, 63b, hereafter referred to as sidearms which are covalently attached to each spacer such that the one sidearm is connected to each side of the spacer's cleavage site 64. The preferred embodiments of the sidearms described herein include oligonucleotides, antibodies and oligonucleotide-antibody conjugates. The assay elements may be used to detect the presence of an analyte and create a signal thereof through either a positive or negative recognition event (FIG. 14). A positive recognition event (FIGS. 14A, C and E) occurs when an analyte 66 binds to both sidearms 63a, 63b resulting in the completion of a connective loop 67 between the two sides the spacer bisected by the cleavage site 64. A negative recognition event (FIGS. 14B, D and F) occurs when analyte 66 binds to only one or neither of the sidearms 68a, 68b and consequently no loop is made connecting the two sides of the spacer. When a positive recognition event is followed by cleavage of the spacers, an unbroken connection from disk to reporter element remains intact (FIG. 14E). On the other hand, cleavage of the spacers in an assay element following a negative recognition event results in the reporter elements being disconnected from the disk (FIG. 14F). Thus, negative recognition results in loose reporter elements that are easily washed away whereas positive recognition results in the reporter elements being retained in their discrete assay sectors. In either case, the results may be observed immediately by CD-ROM or DVD reader.

Further embodiments of the invention are described herein that utilize both reflective or opaque reporter molecules, and positive and/or negative recognition events to carry out a broad range of possible assays. For example, in some assays the sidearms may be connected before a sample is added and binding of the analyte acts to disconnect the sidearms. In this case, a positive recognition event results in the disappearance of the reporter element, while a negative recognition event results in the reporter element being retained.

Other possible embodiments of the assay element described herein do not include cleavable spacers with sidearms. In one such alternative scheme the surface of the IBCD is coated by metal, preferably by gold, and the analyte connects the opaque particles, such as latex beads, or dye loaded liposomes on the metal surface.

Opaque Spheres as Assay Elements

Figure 12A:
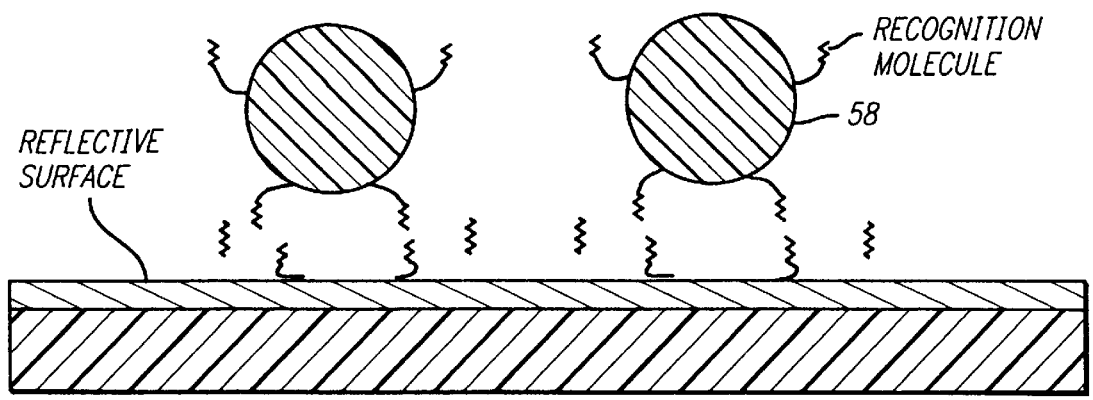
FIGS. 12A–C is a schematic representation of a variation of the detection methodology in which opaque particles are utilized in the place of the reflective particles and bound to a reflective surface. Zig-zag lines represent oligonucleotides, but can be any recognition molecules, such antibodies. Particles are in this example plastic spheres, but can be liposomes, cells, etc.
Figure 12B:
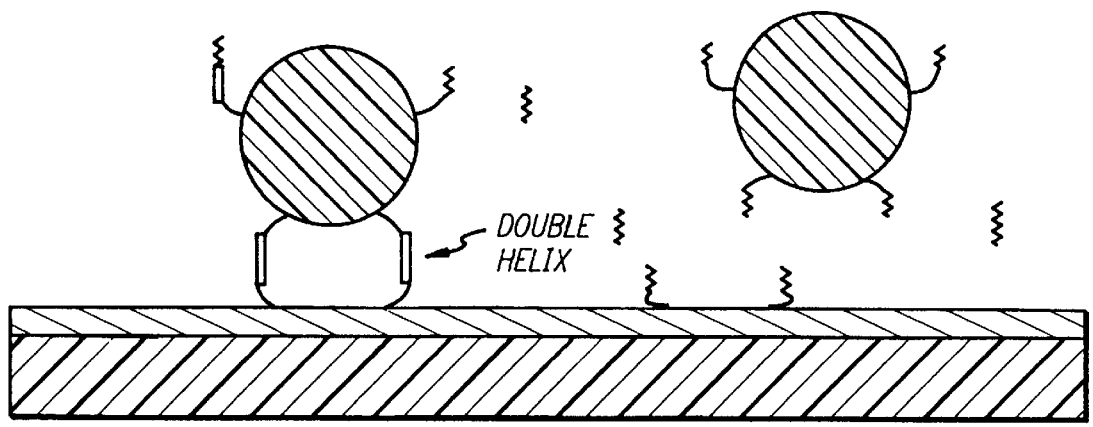
Figure 12C:
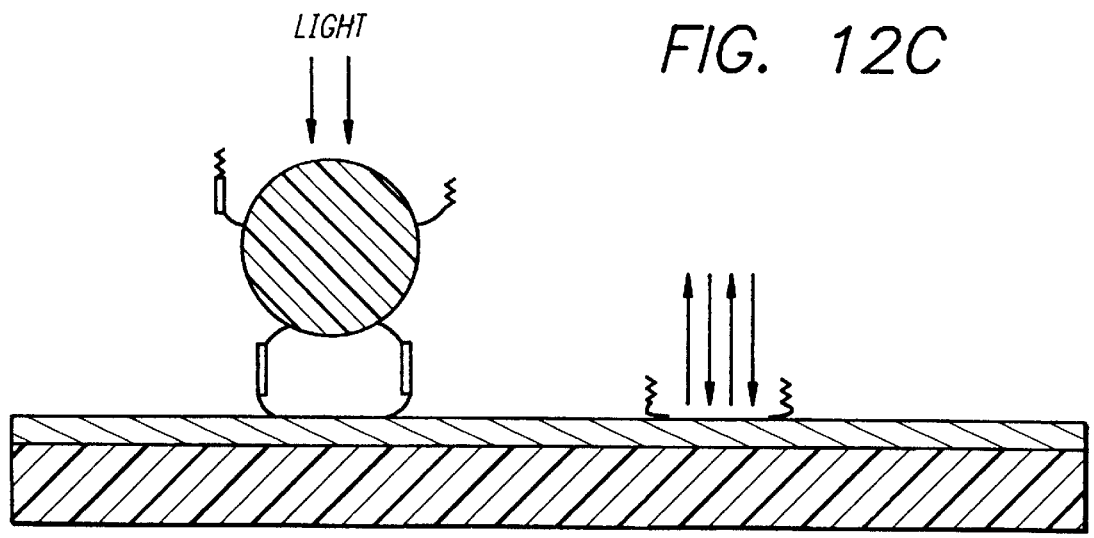

Previous assay elements are based on the binding of reflective particles to the transparent surface of the IBCD. The situation may be reversed so that opaque particles are bound to a reflective surface. This approach is especially advantageous when large cells are assayed and is illustrated generally in FIG. 12.

A metal film is deposited onto the plastic surface. Information may be coded into this metal layer as it is done in conventional CDs. This information may include spatial addresses or other information related to the assay. The metal layer is further covered by a plastic layer. This is then aminated, as described previously, and instead of gold spheres, large latex spheres 58 (10–50 $\mu$m diameter), which contain a dye, are attached to the substrate via spacer molecules as previously described. These latex spheres are partially coated with recognition molecules as described above for gold spheres. Cell recognition binds the latex spheres to the substrate even after the spacers are cleaved, and the dye in the spheres prevents the reflection of the laser light from the metal layer. Alternatively, if a proper fluorescent dye and wavelength of laser light are used, the fluorescent emission of the spheres may be used to monitor the assay. This requires a specialized instrument and will be facilitated by blue lasers when they become available for use in CD-ROM or DVD-readers.

In the simplest version of the cell detection assay, the latex spheres are not connected with the IBCD before the assay, but are added after the cells are bound to the IBCD. The latex sphere suspension is added, the recognition molecules on the spheres bind to the proper cells and these cells are immobilized. These latex spheres may then be observed by reduced reflectance using the CD-ROM or DVD-reader.

Complementary Binding of Spacers

One drawback of the covalent binding of spacers is that the disk is not easily regenerated after the spacers are cleaved. If the spacers are instead connected to the substrate with complementary oligonucleotides, the disk can be regenerated after an assay is completed. The spacers or their residues are removed by heating or by using chaotropic agents. The duplexes that bind spacers are denatured and the disk can be cleaned. The disk retains the oligonucleotides that were binding old spacers. All oligonucleotides on one assay site are identical. They may be different in different assay sites, or they may be identical on the whole IBCD. New spacers having oligonucleotides complementary to those on the IBCD are added. After incubation the complementary oligonucleotides of the spacer and the IBCD hybridize. The excess spacers are washed away. In this case the oligonucleotide sidearms may be attached to the spacers before the spacers are attached to the surface. Gold spheres are then added, they are bound by the thiol groups or disulfide bridges of the spacers, and the disk is ready to be used again.

A cuvette is used for LV/Vis spectrophotometric, fluorescence or chemiluminscence assays. A cuvette in the BCD is basically a capillary that is located between a light source and a photodetector. Light can be guided by mirrors and waveguides. The number of cuvettes in the BCD varies between 0–10,000 and most advantageously between 0–50 per assay sector. The sample arrives into the most cuvettes via a sample preparation chamber. These chambers may contain preloaded reagents or reagents are stored in separate chambers and are mixed with the sample while it arrives into the sample preparation chamber. Sample and reagents may be heated electrically by infrared radiation that is generated by a photodiode. After the incubation period the sample is transferred into the cuvette. The transmitted or emitted light is measured by a photodetector. In this invention the photodetector is most advantageously inside the CD or DVD drive.

Figure 15A:
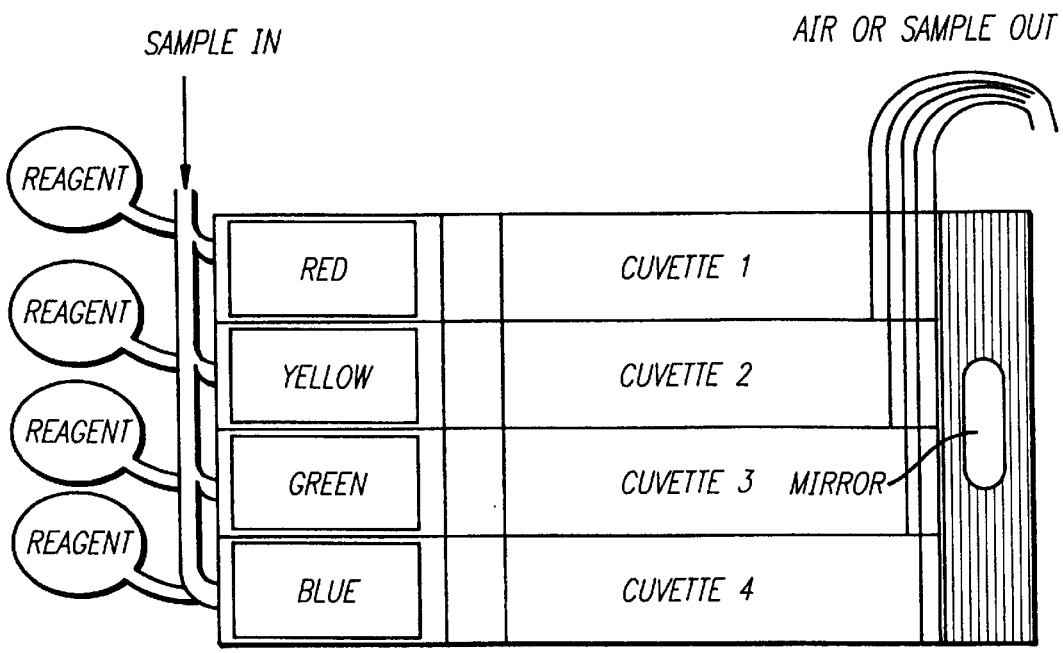
FIG. 15 is a schematic representation of a cuvette assembly. Four cuvettes and their associated reagent and sample preparation chambers as well as light sources are shown in this example.
Figure 15B:
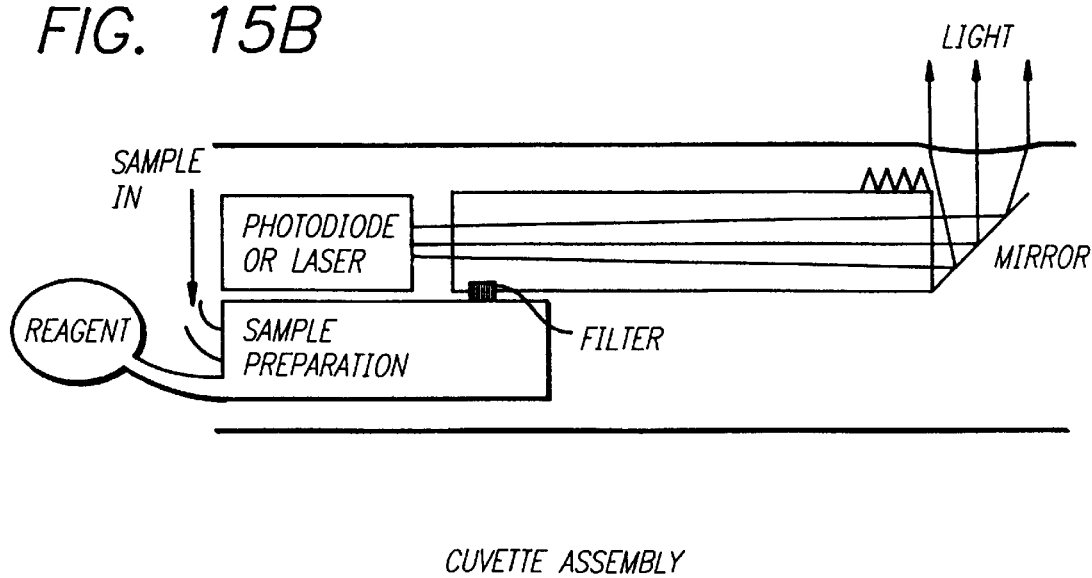

Light sources for spectrophotometric assays are most advantageously photodiodes or semiconductor lasers. It is possible to use the light source of the CD or DVD drive. However, currently these instruments use only one wavelength that corresponds to infrared or red light. If an internal light source of the CD or DVD drive is used, the photodiode or laser in FIG. 15 is replaced by a mirror. Although several assays can be performed by using infrared or red light, it is advantageous for most applications to use additional light sources. For example, an array of photodiodes can be fabricated so that red, yellow, green and blue light can be generated. It is possible to design a photodiode for any given wavelength and accordingly, the number of photodiodes can be up to 300 to cover the whole UV/visible spectral range. Laser generate more power and are better focused than photodiodes and they are preferred. Especially microcavity and nanodot lasers are very small, and they can be fabricated to emit almost any wavelength. The light sources can be fabricated as a module that can be attached onto the disk before and removed after the use of the BCD.

Unit Operations

Next are described the unit operations: centrifugation, filtering, transfer of liquids, mixing of liquids, dialysis, column separations, heating, cooling, electroconvection and electrophoresis.

Centrifugal force is the main force used to transfer liquids in the IBCD. It may also be used for centrifugation, which is important when calls are separated from plasma. In this case, it is advantageous to include a filter with the sample intake container.

In the transfer of liquids, order and timing are important. In order to insure the proper sequence of arrival to a certain reaction site, liquid trains, such as illustrated in FIG. 9, may be created. In one embodiment, two main capillaries, 36 and 37, are provided that are in fluid communication with each other via connecting capillaries 38, 39 and 40. One of the main capillaries is an air channel to allow for fluid flow and typically is rendered hydrophobic. The other main channel carries the reagents in liquid form and typically is hydrophilic. The connecting capillaries and associated cavities may serve to store the reagents, generally designated 41, 42 and 43, and maintain their relative locations with respect to each other. The fluid compartment to which they are directed and their timing of delivery is controlled by their respective locations, the size of the capillaries, the density and viscosity of the fluids and the rotational speed of the disk. The liquids are separated by small air bubbles to prevent mixing, unless mixing is desired. To prevent pressure gradients air capillaries are connected upstream with all liquid capillaries. To further prevent the liquids from entering the air capillaries, these are hydrophobic.

Mixing of two solutions is performed by merging two capillaries in a Y-shaped formation. This alone provides good mixing. To guarantee more efficient mixing a capillary may have small periodic enlargements after the merge. It must be noted that rotation of the IBCD results in efficient mixing in the containers.

In dialysis the liquid is in contact with the membrane containing the buffer. The molecular weight cutoff of the membrane may be chosen to be between 300–500,000 Dalton. Because only a very thin layer of the liquid is in contact with the dialysis membrane, the dialysis is very fast. However, the ratio of the liquid to buffer is only between 1:10 and 1:100 so that the dialysis is not quantitative. For most purposes it is sufficient.

Gel, adsorption and ion exchange chromatographies are all possible. The various molecular species are fractionated by the chromatographic media and exit the capillary separately as in conventional chromatography. Using a valve, certain fractions may be selected and guided into an assay element.

Heating is best done electrically. Upper and lower electrodes are separated by about 500 μm. If the solution contains ions, the system is virtually short circuited and heats up. Heating may be terminated by removing ions either from the battery or from the container. Constant temperature can be achieved by including a thermostat into the circuitry. A bimetallic element is a very simple thermostat that can close a circuit below a preset temperature and open it at higher temperature. Another heating mechanism is provided by the laser of the CD or DVD-drive. Especially, CD-R-drives have powerful lasers. Either the top or the bottom of the cavity can have a liquid crystalline film that is isolated by a transparent layer, if necessary. On the other side of the cavity is a reflective layer. When the temperature of the cavity is below the main transition temperature the liquid crystal will scatter the light and no reflection is observed. Above the main transition temperature the light is reflected back and the heating can be discontinued and it is less effective anyway. Cooling is preferably provided by endothermic dissolution, i.e., the absorption of heat by the presence of a dissolving substance. The cooling solution and the solution to be cooled should be separated by a thin aluminum, copper, silver or gold film. Cooling may also be produced by passive air cooling. This method cools only to ambient temperature, but for most purposes this is enough. Cooling and heating may also be alternated in a cyclical fashion, either in one cavity or in a serially alternating sequence of heating and cooling cavities. This allows PCR amplifications to be performed inside the IBCD.

Figure 16:
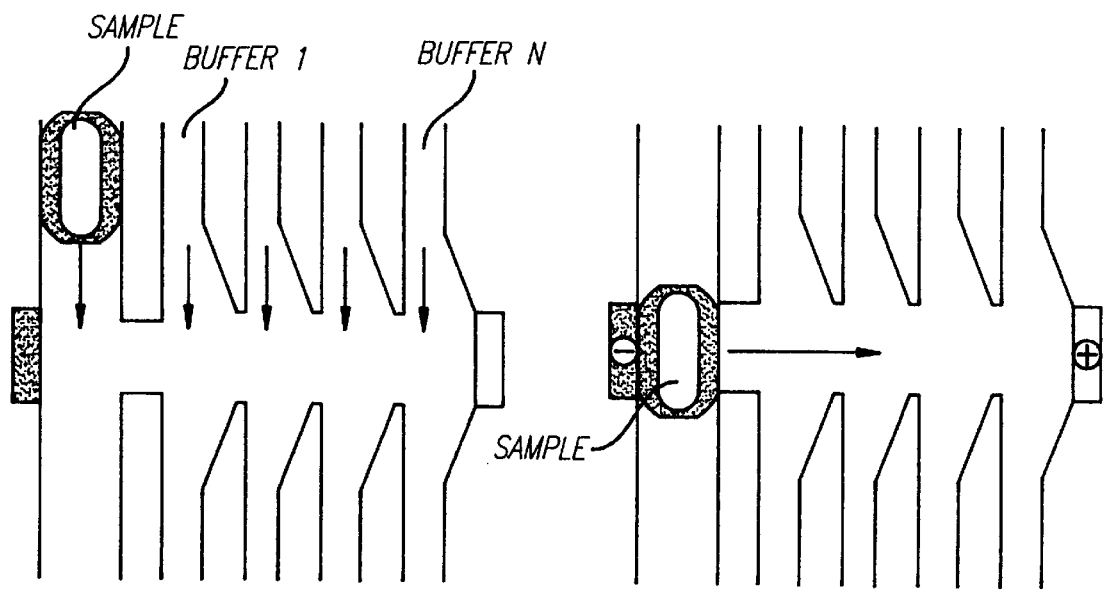
FIG. 16 is a schematic representation of a capillary array that can be used to perform isoelectric focusing.
Figure 16:
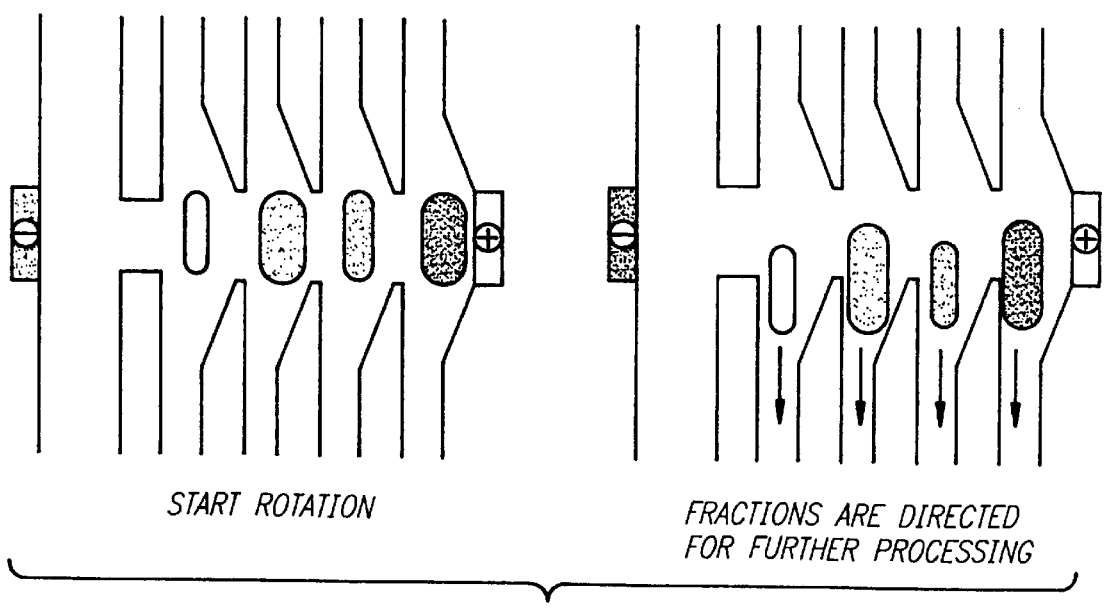

Electroconvection, electrophoresis and isoelectric focusing may each be utilized in particular applications. In electroconvection the material is transferred without trying to separate it into components. In electrophoresis the separation is the main purpose. The separation is facilitated by the use of a gel that prevents convection. Because distances are very short, the available field strength is sufficient for proper electrophoresis. For the same reason the necessary time for separation is fairly short and may be on the order of 1–5 minutes, or even less than 1 minute. Useful electroconvection may be performed in few seconds. Isoelectric focusing is basically electrophoresis in a pH gradient. A pH gradient may be created by an array of parallel capillaries, each of which contains a different buffer so that the pH changes gradually. This is demonstrated in FIG. 16. A large part of the buffer will remain in the capillaries and this will guarantee the existence of the pH gradient during the isoelectric focusing. After the focusing is completed the components can be moved along the capillaries by centrifugal force or an orthogonal electrophoresis can be performed. This method allows almost complete fractionation of human plasma proteins (Anderson, Tracy and Anderson, "The Plasma Proteins," $2^{nd}$ Ed., Vol. 4, Academic Press, Inc., 1984).

A particularly advantageous configuration of an assay site is illustrated in FIG. 10. The assay element contains the spacer molecules and the reflective spheres as described previously but does so in a linear array that may be conveniently located in one or more of the capillary channels at the assay site of the disk. As has been described, analyte binds to the spacer molecules that have side arms receptive to or complementary to the analyte (as illustrated in A) and after washing the analyte that has bound is located at specific locations of the array (as illustrated in B). The presence of the bound analytes is determined by conventional address determination as with conventional compact disk readers and associated software as has been described.

EXAMPLE 1

Assay Sector for Oligonucleotide Analysis (FIG. 2, Assay Sector)

A sample that contains DNA is mixed with sodium dodecyl sulfate to lyse the cells. This solution is transferred into the container denoted "Sample in" and the disk is rotated. The sample is filtered and mixed with a mixture of complementary oligonucleotides. These oligonucleotides are complementary to those to be analyzed and also have a thiol group at one end. Hybridization is allowed to proceed in the container denoted "Sample prep." Optionally, this container may be heated (not shown in Figure). After appropriate incubation, the disk is rotated. While the sample is transferred into the container denoted "Sample sep." it is mixed with a nuclease S solution delivered from a side capillary. The mixture is allowed to incubate in the "Sample sep." container which has two gold electrodes and a valve as has been illustrated in FIG. 8. The lower electrode is coated with spacers having isothiocyanate end groups. These bind to the thiol containing oligonucleotides several of which are hybridized with the sample. All unhybridized parts of DNA are digested and washed away. The battery then becomes operational. This is adjusted by the speed by which the acid and copper ions flow into the empty battery. The container heats up, the bound oligonucleotides are released and the valve is switched.

The oligonucleotides are flushed into the assay area. After suitable incubation the ligase arrives into the assay area and the two sidearms on the spacer molecule are connected, if the sample contains the proper oligonucleotide. The labile spacers are cut. If spacers contain siloxane groups the cutting is done by addition of fluoride ions. The loose gold spheres are washed away by rotating the IBCD at high speed. Reading may be performed immediately.

EXAMPLE 2

Assay Element for the Detection of Cells and Viruses

Figure 11A:
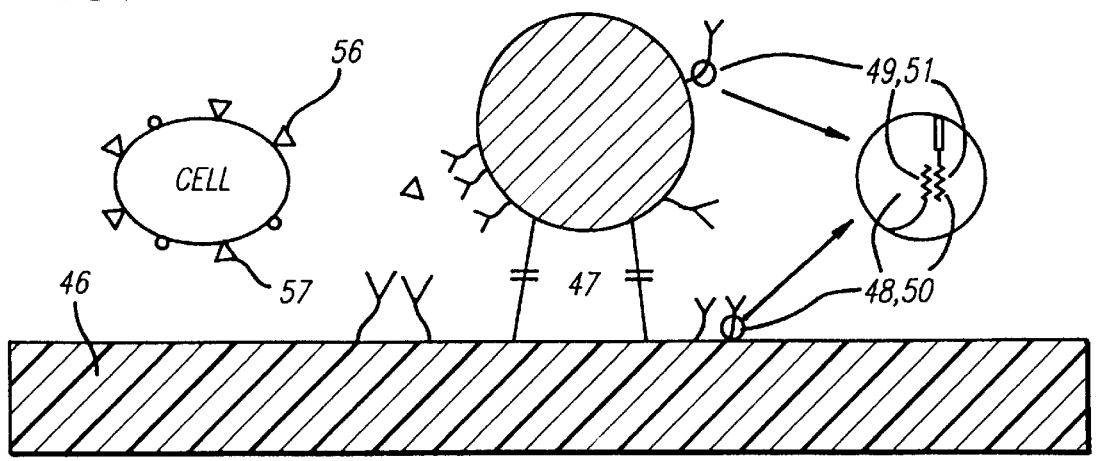
FIGS. 11A–C is a schematic representation of a variation of an assay element that is particularly useful for the detection of viral and bacterial particles and cells using the general methodology of site specific localization of the substance to be detected.
Figure 11B:
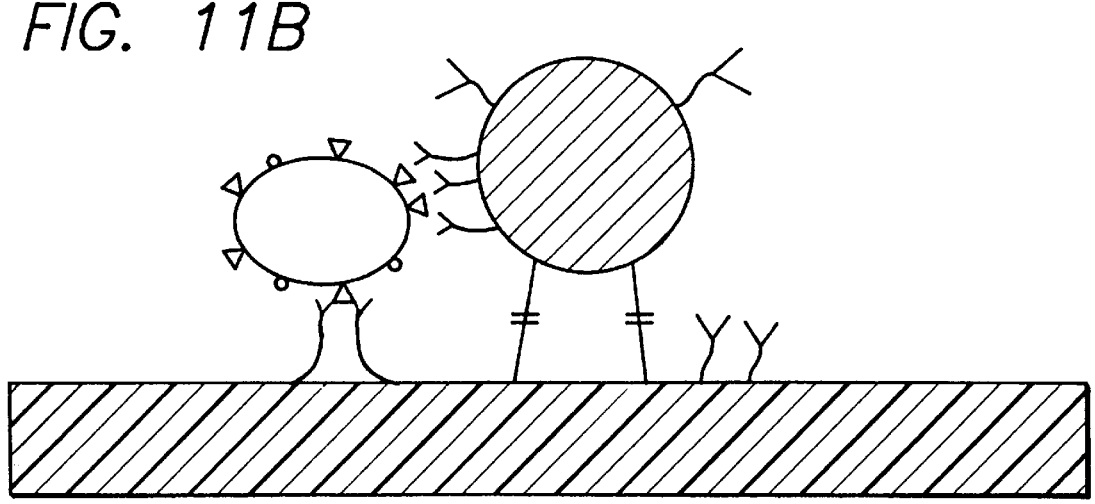
Figure 11C:
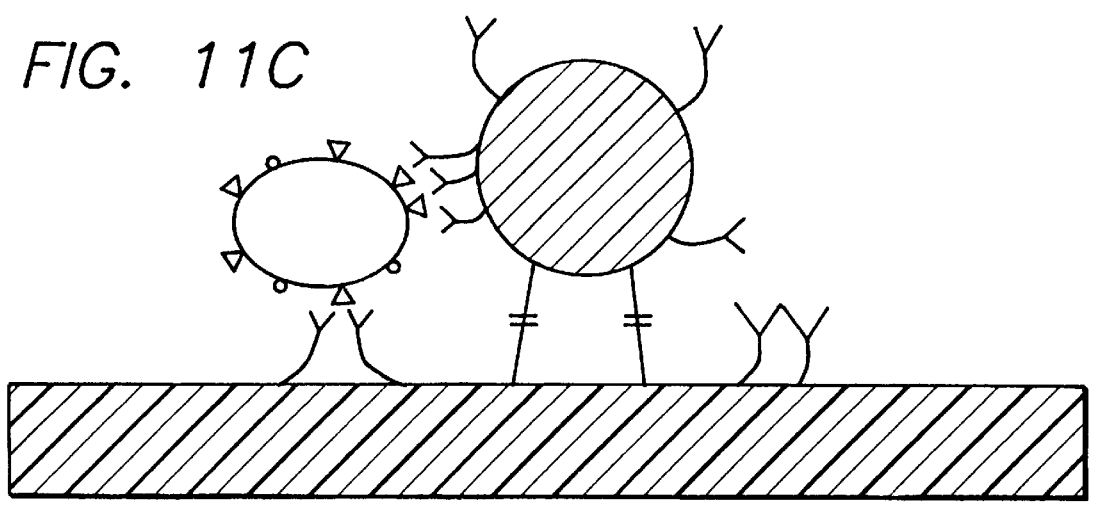

Alternative embodiments of the assay element described elsewhere herein are useful for the detection of viral and bacterial particles, cells and other particles that are larger than the oligonucleotides, antibodies, antigens and the like that have been described previously. Viruses are typically nearly spherical particles having a diameter less than 0.5 $\mu$m. Bacteria are commonly either spherical or rod shaped. Their largest dimension is less than 2 $\mu$m excluding flagella and other similar external fibers. These pathogens are smaller or about the same size as the gold spheres used to detect them, and their interaction with two sidearms of the spacer may be limited. For this reason these sidearms are connected with the surface of the IBCD and the gold sphere instead of with the spacer as illustrated in FIG. 11. The gold sphere is attached to a spacer molecule 45 at one end of the spacer molecule and the other end of the spacer is attached to the surface of the substrate 46. The spacer molecule is provided with a typical cleavage site 47, for example a siloxane moiety, as has been previously described. In contrast to prior described embodiments where the side-arms are attached to the spacer molecule between the substrate and the cleavage site and the gold sphere and the cleavage site, side arms are attached to the gold sphere and to the surface of the substrate. For illustration purposes, in FIG. 11 oligonucleotides 48 and 49 are attached to the surface of the substrate and oligonucleotides 50 and 51 are attached to the surface of the gold sphere. Then complementary oligonucleotides are conjugated with members of a specific binding pair, designated as 52, 53, 54, and 55 are attached to the oligonucleotides on the substrate and the gold sphere as illustrated. This gives much more space for the cells to bind with the antibodies or other recognition molecules.

The spacers each still have at least one cleavage site. They are, in all respects identical to those described previously except that they have no attached sidearm molecules. When the cell for example arrives at the assay site, if it contains moieties that form specific binding pairs with their respective complementary members, a connective loop is formed between the gold sphere and the substrate. When the spacer molecule is cleaved, the gold sphere is retained on the substrate and the presence of the cell may be detected as previously described. However, if no specific binding pairs are formed, upon cleavage of the spacer, the gold sphere does not remain attached to the substrate and is removed.

Antibodies or other recognition molecules may be attached to the substrate in a manner similar to that with which the spacers are attached. All spacers on the IBCD are identical and are attached at the same time to the amino groups or analogous active groups on the surface. About half of the amino groups are used for the attachment of the spacers. The other half is used to couple recognition molecules to the substrate. If all recognition molecules on the surface of the IBCD are similar, they may be attached at the same time as spacers. Alternatively, if the recognition molecules are specific for each assay site, they may be dispensed locally by contact printing, ink-jet printing or microcapillary deposition.

After the gold spheres are attached to the thiol groups in the spacers, the other recognition molecules are attached, also via thiol groups, to the gold spheres. For this purpose these recognition molecules are first conjugated with a spacer containing a protected thiol or amino group. The amino group may be derivatized so that a thiol group is introduced. The various recognition molecules to be attached to the gold spheres are dispensed in a manner similar to that with which the other recognition molecules were attached with the surface of the IBCD.

The recognition molecules may be oligonucleotides. These oligonucleotides may be further hybridized with complementary oligonucleotide-biomolecule conjugates. This approach allows attachment of sensitive and reactive biomolecules, for example, proteins containing several amino or thiol groups.

The recognition molecules bound to the gold spheres are free to diffuse around the sphere although they are tightly bound. The cell that is recognized by both recognition molecules completes a connective loop that binds the gold sphere to the surface of the IBCD. After cleaving the spacer, the gold sphere is retained and detected by the CD-ROM or DVD reader.

A multiplicity of different recognition molecules in the same assay site may be used. The advantage of this approach is that all known mutants of a certain pathogen species may be detected on one assay site. The various mutants also may be characterized on different assay sites containing specific recognition molecules.

The IBCD is a universal analyzer. It is easy to use and in its most advanced form it contains all reagents and only the sample is added. It can be used in clinical laboratories, hospitals, doctors' offices, and in the home. In home use the information can be loaded into a doctor's office via the internet. The IBCD can be designed so that the genetic signature of each patient is measured every time. About 35 polymorphism points are enough to give every person a unique "bar-code". This eliminates possible mistakes due to mixing of tubes or labels. Assays that can be performed include, but are not limited to immunoassays, DNA testing, cell counting and cell shape measurement, detection of cancerous cells in tissue samples, blood chemistry and electrolyte analysis. Other applications include mass screening of drug candidates, food and environmental safety analysis, and monitoring pathogens and toxins in a battlefield.

EXAMPLE 3

Turbidimetric Assay of Lipase Activity

Figure 17:
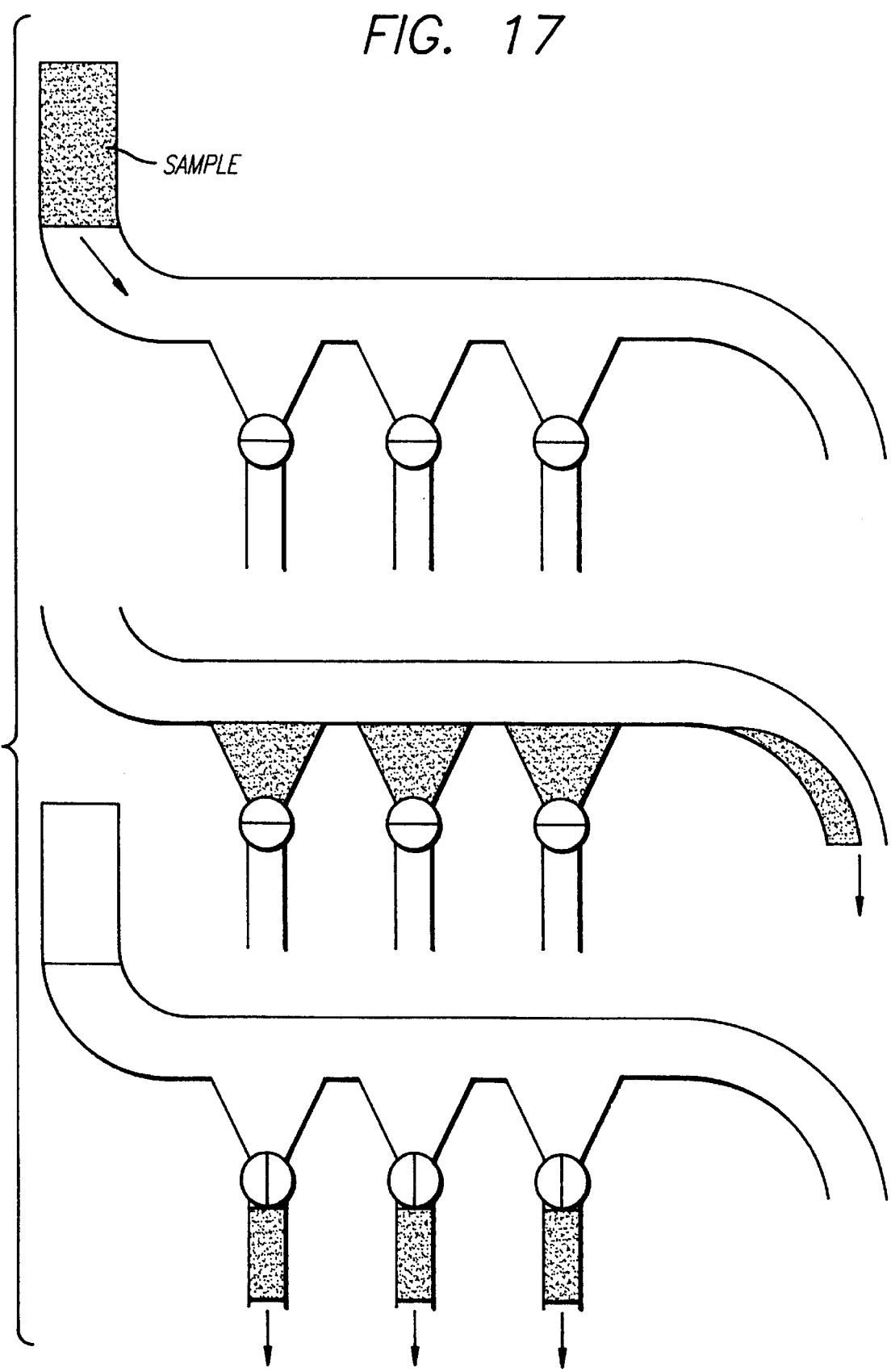
FIG. 17 is a schematic representation of an apparatus for measuring exact volumes.

The reagent cavity contains 15 $\mu$L of stabilized triolein (250 $\mu$M) emulsion that contains sodium deoxycholate (30 mM) and $CaCl_2$ (100 $\mu$M) at pH 9.0 in TRIS buffer (25 mM). The sample preparation chamber contains lyophilized porcine colipase (0.5 $\mu$g). Two microliters of serum is taken into the sample preparation chamber (using apparatus as shown in FIG. 17) together with stabilized triolein and other reagents. Part of the mixture (5 $\mu$L) is further transferred into a cuvette. Because the exit capillary goes toward the center of the disk, the counterpressure will prevent further flow. Absorbance at 340 mn is read at one minute intervals. The $\Delta A$/min is a measure of lipase activity.

While this invention has been described with respect to some specific embodiments, it is understood that modifications thereto and equivalents and variations thereof will be apparent to one skilled in the art and are intended to be and are included within the scope of the claims appended hereto.

What is claimed is:

1. An optical disk, adapted to be read by a CD-ROM or a DVD reader and wherein the reader is adapted to be coupled to an information processor, comprising a first sector having a substantially self-contained assay means for binding or reacting an analyte suspected of being in a sample to at least one, predetermined location in the first sector and optionally a second sector containing a control means for conducting the assay and analyte location information with respect to one or more analytes suspected of being in a sample, accessible to a reader, and wherein the presence or absence of the analyte at said location is determinable by the reader using the control means and the location information and a sample entry port.

2. The optical disk of claim 1 wherein the sample entry port is in fluid communication with the assay means.

3. An apparatus for conducting an assay comprising an optical disk, a CD-ROM or DVD disk reader and an information processor, wherein the disk comprises a sample entry port, a first sector having a substantially self-contained assay means for binding an analyte suspected of being in a sample to at least one, predetermined location in the first sector and optionally a second sector containing control information for conducting the assay and analyte location information with respect to one or more analytes suspected of being in the sample, accessible to the reader and processable by the information processor, wherein the disk is adapted to be read by the reader and the information processor is adapted to determine the presence or absence of the analyte at said location using the control information and the location information.

4. The apparatus of claim 3 wherein the reader is adapted to be coupled to an information processor.

5. The apparatus of claim 3 wherein the information processor is a personal computer.

6. The disk of claim 1 wherein the assay means comprises a fluid storage means and a fluid transfer means formed in a disk surface.

7. The disk of claim 6 wherein the fluid transfer means comprises a capillary duct.

8. The disk of claim 7 wherein the fluid transfer means comprises a valve.

9. The disk of claim 6 wherein the disk comprises an electrochemical energy means.

10. The disk of claim 1 wherein the assay means comprises a sample port, a sample preparation sector, an analyte separation sector and an assay sector wherein the analyte is localized.

11. The disk of claim 6 wherein the fluid transfer means is responsive to centrifugal force or an electric field.

12. The disk of claim 1 wherein the disk comprises a multiplicity of first sectors adapted to analyze for a multiplicity of analytes.

13. The disk of claim 1 further comprising a multiplicity of first sectors adapted to analyze for the same analyte or different analytes wherein each of said multiplicity of sectors is adapted for fluid communication to a sample port.

14. An assay component adapted to be read by a CD-ROM or a DVD reader comprising an optical disk having a sample entry port and a substantially self-contained assay means in the disk for binding an analyte suspected of being in a sample to at least one, predetermined location on the disk and means at said location for enabling detection of the absence or presence of the analyte by the CD-ROM or the DVD reader.

15. An optical disk, adapted to be read by a CD-ROM or a DVD reader comprising a sample entry firs a substantially self-contained assay means for localizing an analyte suspected of being in a sample to at least one, predetermined location on the disk and a means at said location for detecting the absence or presence of the analyte by the CD-ROM or the DVD reader.

* * * * *

UNITED STATES PATENT AND TRADEMARK OFFICE
CERTIFICATE OF CORRECTION

Figure 2A:
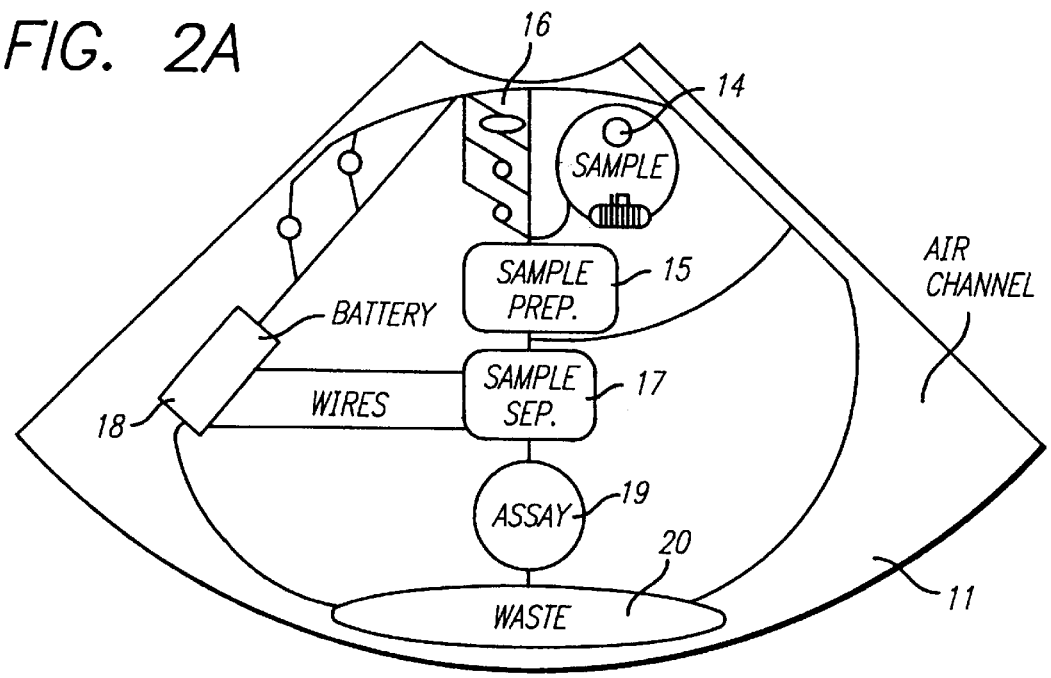
FIG. 2A is a more detailed schematic representation of a sample preparation and assay sector of the disk, illustrating the overall layout of a typical assay sector.

PATENT NO.  : 6,030,581
DATED       : February 29, 2000
INVENTOR(S) : Jorma Virtanen It is certified that error appears in the above-identified patent and that said Letters Patent is hereby corrected as shown below:

In the Drawings:

Fig. 2A    the reference line for "AIR CHANNEL" should extend to the left in the figure and terminate at the curved line which extends upwardly from the oval 20 entitled "WASTE".

Figure 2B:
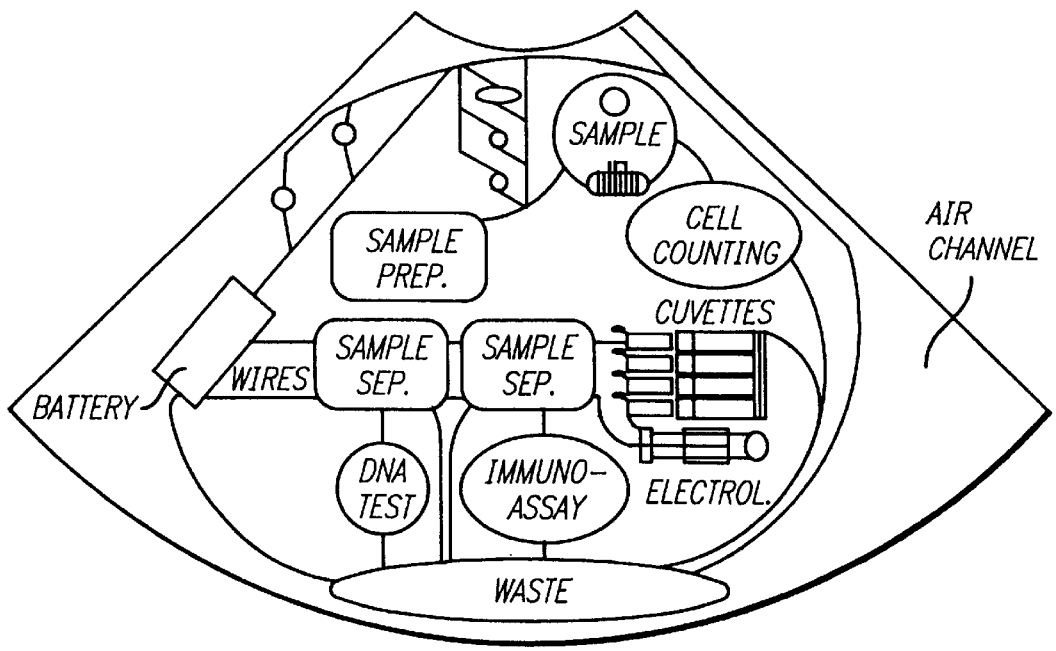
FIG. 2B is a schematic representation of an ubiquitous assay sector that is capable of performing immunoassays, DNA testing, cell counting, spectrophotometric assays and electrolyte analysis.

Fig. 2B    the reference line for "AIR CHANNEL" should extend to the left in the figure and terminate at the curved line which extends upwardly from the oval entitled "WASTE". There should be a line between the "SAMPLE PREP." rectangle and the "SAMPLE SEP." rectangle Column 1,
Line 6, after "1997" insert --, now --

Column 3,
Line 50, change "14a" to -- 14A --
Line 53, change "14b" to -- 14B --
Line 56, change "14c" to -- 14C --
Line 57, change "14a" to -- 14A --
Line 60, change "14d" to -- 14D --
Line 61, change "14b" to -- 14B --
Line 64, change "14e" to -- 14E -- and delete "(leftmost)"
Line 65, change "14c" to -- 14C --

Column 4,
Line 1, change "14f" to -- 14F -- and delete "(rightmost)"
Line 2, change "14d" to -- 14D --

Column 5,
Line 26, delete "at"

Column 7,
Line 4, change "place" to -- placed --

Column 13,
Line 38, delete "and 49 are" and insert -- is --
Line 39, delete "50 and 51 are" and insert -- 47 is --
Line 42 delete "52, 53, 54," and insert -- 50, --; delete "55" and insert -- 51 --

UNITED STATES PATENT AND TRADEMARK OFFICE
CERTIFICATE OF CORRECTION

PATENT NO. : 6,030,581
DATED : February 29, 2000
INVENTOR(S) : Jorma Virtanen

It is certified that error appears in the above-identified patent and that said Letters Patent is hereby corrected as shown below:

Column 16,
Line 32, which is second line of Claim 15, delete "firs" and insert -- port, --.

Signed and Sealed this

Fourteenth Day of August, 2001

*Attest:*

NICHOLAS P. GODICI
*Attesting Officer*    *Acting Director of the United States Patent and Trademark Office*